US006936465B1

(12) United States Patent
Katsumata et al.

(10) Patent No.: US 6,936,465 B1
(45) Date of Patent: Aug. 30, 2005

(54) PLASMID VECTOR COMPRISING A RETROVIRAL INTEGRASE GENE AND AN INTEGRASE RECOGNITION REGION

(75) Inventors: Atsushi Katsumata, Tokyo (JP); Sumio Hoshi, Tokyo (JP); Takeshi Ihara, Tokyo (JP); Susumu Ueda, Saitama (JP)

(73) Assignee: Nippon Institute for Biological Science, Tokyo (JP)

( * ) Notice: Subject to any disclaimer, the term of this patent is extended or adjusted under 35 U.S.C. 154(b) by 0 days.

(21) Appl. No.: 09/762,568

(22) PCT Filed: Apr. 27, 2000

(86) PCT No.: PCT/JP00/02785

§ 371 (c)(1),
(2), (4) Date: Jul. 30, 2001

(87) PCT Pub. No.: WO00/75342

PCT Pub. Date: Dec. 14, 2000

(30) Foreign Application Priority Data

Jun. 4, 1999 (JP) ............................................ 11-158351

(51) Int. Cl.[7] ....................... C12N 15/63; A01K 67/027
(52) U.S. Cl. ........................ 435/320.1; 435/69.1; 800/8
(58) Field of Search ............................ 435/320.1, 69.1; 800/8

(56) References Cited

FOREIGN PATENT DOCUMENTS

WO WO 96/04386 2/1996
WO WO 96/37626 11/1996
WO WO 97/07223 A1 * 2/1997

OTHER PUBLICATIONS

Pereira et al. A compilation of cellular transcription factor interactions with the HIV-1 LTR promoter. Nucleic Acids Res. Feb. 1, 2000; 28(3):663–8.*
Ivarie R. Avian transgenesis: progress towards the promise. Trends Biotechnol. Jan. 2003;21(1):14–9.*
Houdebine L.M. Transgenic animal bioreactors. Transgenic Res. 2000;9(4–5):305–20.*
Emanueli et al. Angiogenesis gene therapy to rescue ischaemic tissues: achievements and future directions. Br J Pharmacol. Aug. 2001;133(7):951–8.*
Rissanen et al. Gene therapy for therapeutic angiogenesis in critically ischaemic lower limb—on the way to the clinic. Eur J Clin Invest. Aug. 2001;31(8):651–66.*
Schwaab et al. Gene therapy of hemophilia. Semin Thromb Hemost. Aug. 2001;27(4):417–24.*
Rubanyi G.M. The future of human gene therapy. Mol Aspects Med. Jun. 2001;22(3):113–42.*
Ross et al. Gene therapy in the United States: a five–year status report. Hum Gene Ther. Sep. 10, 1996;7(14):1781–90.*
Marshall E. Gene therapy's growing pains. Science. Aug. 25, 1995;269(5227):1050, 1052–5.*
Verma et al. Gene therepy—promises, problems and prospects. Nature. Sep. 18, 1997;389(6648):239–42.*
Doetschman T. Interpretation of phenotype in genetically engineered mice. Lab Anim Sci. Apr. 1999;49(2):137–43.*
Sigmund C.D. Viewpoint: are studies in genetically altered mice out of control? Arterioscler Thromb Vasc Biol. Jun. 2000;20(6):1425–9.*
Wall (1996) Theriogenology 45:57–68.*
Orkin et al. (1995) Report and recommendations of the panel to assess the NIH investment in research on gene therapy, Available through NIH or at http://www.nih.gov/news/panelrep.html.*
Eck et al. (1996) Goodman & Gilman's The Pharmacological Basis of Therapeutics, 9th Edition, Chapter 5, McGraw–Hill, NY.*
Panganiban (1983, Nature, vol. 306, p. 155–160.*
Vick (1993, Proc. R. Soc. Lond., vol. 251. p. 179–182.*
Yeong Ho Hong et al., "Improved transfection efficiency of chicken gonadal primordial germ cells for the production of transgenic poultry"; Transgenic Research vol. 7, pp. 247–252 (1998).
Lorraine Vick, et al., "Transgenic birds from transformed primordial germ cells", Proc. R. Soc. Lond. B. Biol. Sci., vol. 251, pp. 179–182 (1993).
Patrick O. Brown, et al., "Retroviral integration. Structure of the initial covalent product and its precursor, and a role for the viral IN protein", Proc. Natl. Acad. Sci. USA vol. 86, pp. 2525–2529 (Apr. 1989).
Antonio T. Panganiban, et al., "Circles with Two Tandem LTRs Are Precursors to Integrated Retrovirus DNA", Cell, vol. 36, pp. 673–679 (Mar. 1984).
G Duyk, et al. "Circles with Two Tandem Long Terminal Repeats Are Specifically Cleaved by pol Gene–Associated Endonuclease from Avian Sarcoma and Leukosis Viruses Nucleotide Sequences Required for Site–Specific Cleavage", Journal of Virology, vol. 56, No. 2, pp. 589–599 (1985).
Akiko Shoji–Tanaka, et al., "*Gene Transfer Using Purified Retroviral Integrase*", Biochemical and Biophysical Research Communications, vol. 203, No. 3, pp. 1756–1764 (1994).
Makota Mochii, "Transgenic Birds", Tanpakushitsu Kakusan Kouso (Proteins, Nucleic Acids, and Enzymes), vol. 40, No. 14, pp. 277–285 (1995).

(Continued)

*Primary Examiner*—David Guzo
*Assistant Examiner*—Daniel M. Sullivan
(74) *Attorney, Agent, or Firm*—Knobbe Martens Olson & Bear, LLP

(57) ABSTRACT

A plasmid vector having components (D1), (D2), and (D3) enables the efficient integration of foreign DNA into host cells. The components are (D1) an integrase gene, (D2) a segment of DNA forming a region for controlling the expression of the integrase gene, and (D3) a segment of DNA serving as an integrase recognition region when integrase catalyzes the integration reaction.

6 Claims, 25 Drawing Sheets

OTHER PUBLICATIONS

Padmini Kedar, et al., "Nucleotide Sequence of the Integrase (IN) Gene of an Endogenous Murine Leukemia Retroviral DNA", Nucleic Acids Research, vol. 18, No. 13, p. 4022 (1990).

Paul J Hippenmeyer, et al., "Requirement of the Avian Retrovirus pp32 DNA Binding Protein Domain for Replication", Virology, vol. 137, pp. 358–370 (1984).

Dennis E Schwartz, et al., "Nucleotide Sequence of Rous Sarcoma Virus", Cell, vol. 32, pp. 853–869, (Mar. 1983).

Stephen H. Hughes, et al., "A Rous Sarcoma Virus Provirus is Flanked by Short Direct Repeats of a Cellular DNA Sequence Present in Only One Copy Prior to Integration", Proc. Natl. Acad. Sci. USA, vol. 78, No. 7, pp. 4299–4303 (Jul. 1981).

Richard A. Katz, et al., "The Avian Retroviral IN Protein Is Both Necessary and Sufficient for Integrative Recombination In Vitro", Cell, vol. 63, pp. 87–95, (Oct. 1990).

Michael Katzman, et al., "In Vitro Activities of Purified Visna Virus Integrase", Journal of Virology, vol. 68, No. 6, pp. 3558–3569, (Jun. 1994).

GenBank: accession No. AF110968, x94150 (Dec. 12, 1995).

GenBank: accession No. AF110968, Y07725 (Oct. 8, 1996).

Surend T. Nath, et al., "Function of Two Discrete Regions Is Required for Nuclear Localization of Polymerase Basic Protein 1 of A/WSN/33 Influenza Virus (H1 N1)", Molecular and Cellular Biology, vol. 10, No. 8, pp. 4139–4145 (Aug. 1990).

Daniel Kalderon, et al., "A Short Amino Acid Sequence Able to Specify Nuclear Location", Cell, vol. 39, pp. 499–509 (Dec. 1984).

Shyoso Ogawa, et al., "Gene Expression in Blastocysts Following Direct Injection of DNA into Testis", Journal of Reproduction and Development, vol. 41, pp. 379–382 (1995).

Shinji Mizuarai, et al., "Integrase–Mediated Nonviral Gene Transfection with Enhanced Integration Efficiency", Journal of Bioscience and Bioengineering, vol. 88, No. 5, pp. 461–467 (1999).

* cited by examiner

RESTRICTION ENZYME

Bg :BglII
E :EcoRI
Rv :EcoRV
Hc :HincII
H :HindIII
Rs :Rsal
S :SalI
V :VspI

```
HindIII Cassette   1                                        TCGTTAGAACGCGTAATACGACTCACTATAGGGGA                            36
clone 1            1   TCGTTAGAACGCGTAATACGACTCACTATAGGGGAAGCTTGAGGAAATGCAGGGACTGTG    60
clone 2            1   TCGTTAGAACGCGTAATACGACTCACTATAGGGGAAGCTTTATGTGTCCGATGTTTGCA    60
clone 3            1   TCGTTAGAACGCGTAATACGACTCACTATAGGGGAAGCTTAACCAACACATCAACCCA     60
clone 4            1   TCGTTAGAACGCGTAATACGACTCACTATAGGGGAAGCTTCACACTTTTAATTGAGAGC   60

HindIII Cassette   36  CATTGACTTGCCAGGAGGCTGAGGGCAAAGGTTTCCGTTGCCTGCACCAGCTGGGATGCC  120
clone 1            61  CTTGAAGGATAGACGTGTGGATCTAGAGAGTAATGGCTGTTTTCTCCTCTGATGTTT     120
clone 2            61  TCNTTTTTAGTCAGTCACACGTTTGAACCTTTCATGAACTGTTTCAAGAAGCTTTC      120
clone 3            61  CTTCTGGTTTATGTAGAAGAATCCAGACATCCTTTTGGTTTAGAATGCACTTCTAGCCCT  120
clone 4            61

HindIII Cassette   121 CTGTGCTCCTGGGATGTGTGAT                                         142
clone 1            121 GCAGGTGATAACATGTACAGCT                                         142
clone 2            121 CTG                                                            123
clone 3            121 CAGGGCAGCAGATTAAAT                                             138
clone 4
```

FIG. 13

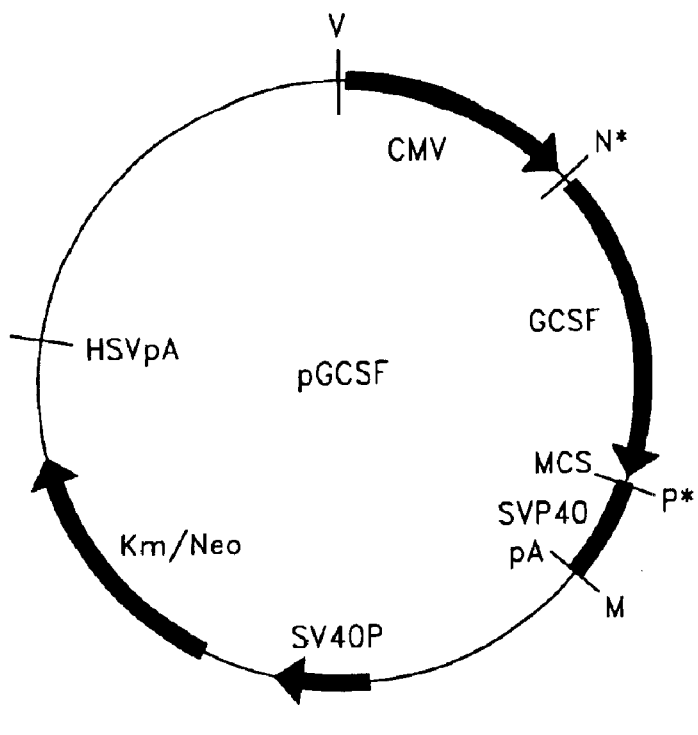
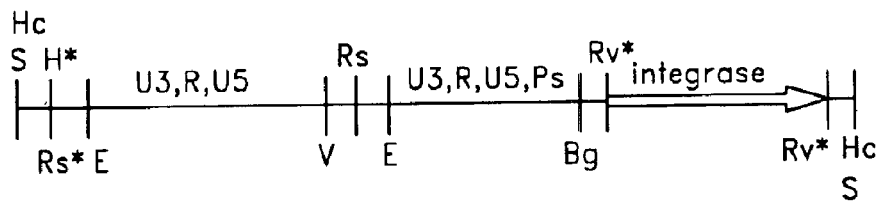
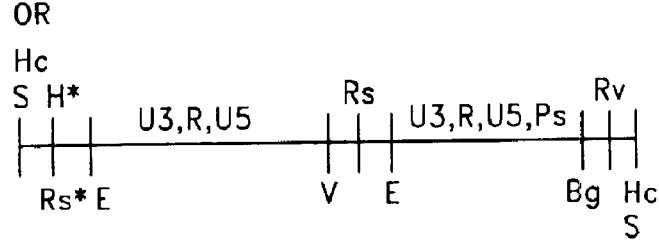
FIG. 16

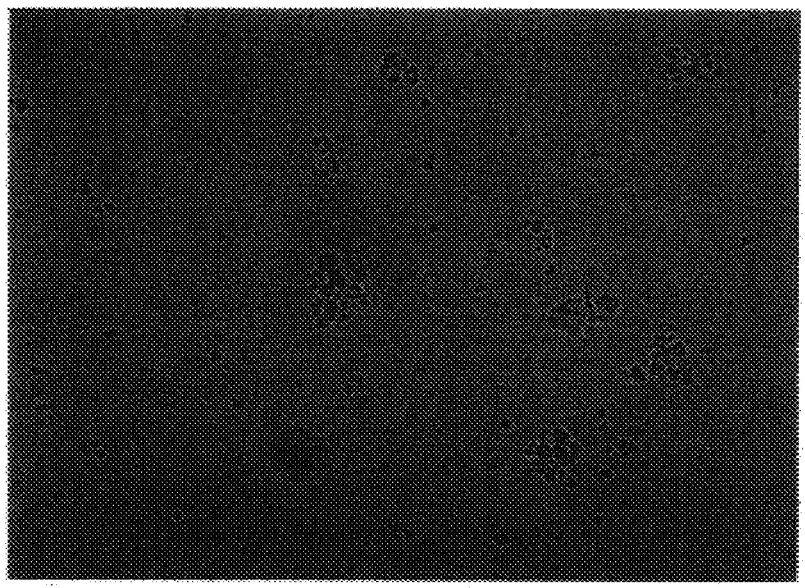
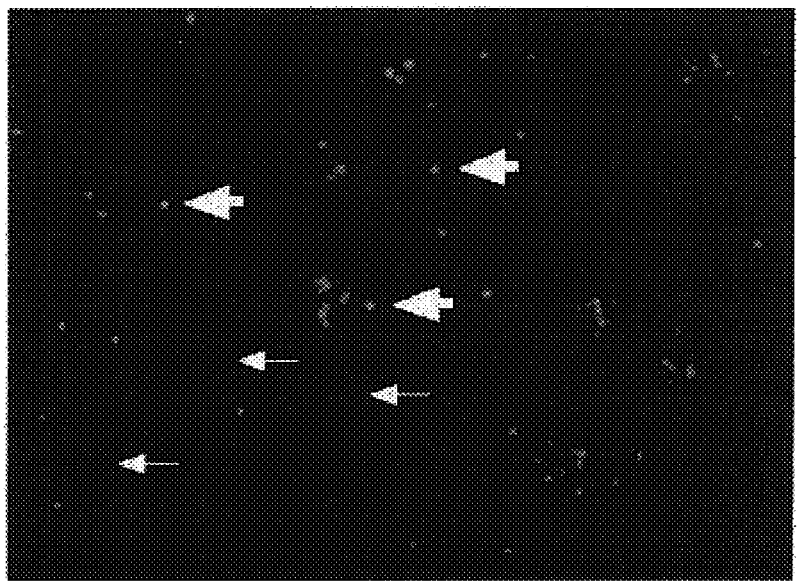
(NOTE) ◄ "BOLD ARROW" INDICATES TYPICAL GFP POSITIVE CELLS
◄ "NORMAL ARROW" INDICATES TYPICAL GFP NEGATIVE CELLS
FIG.20

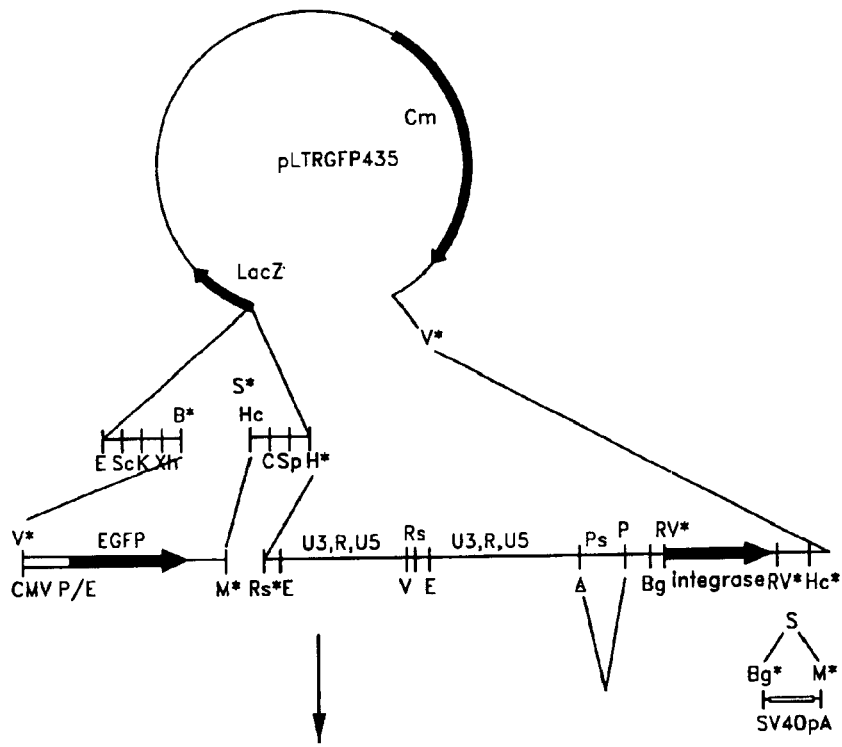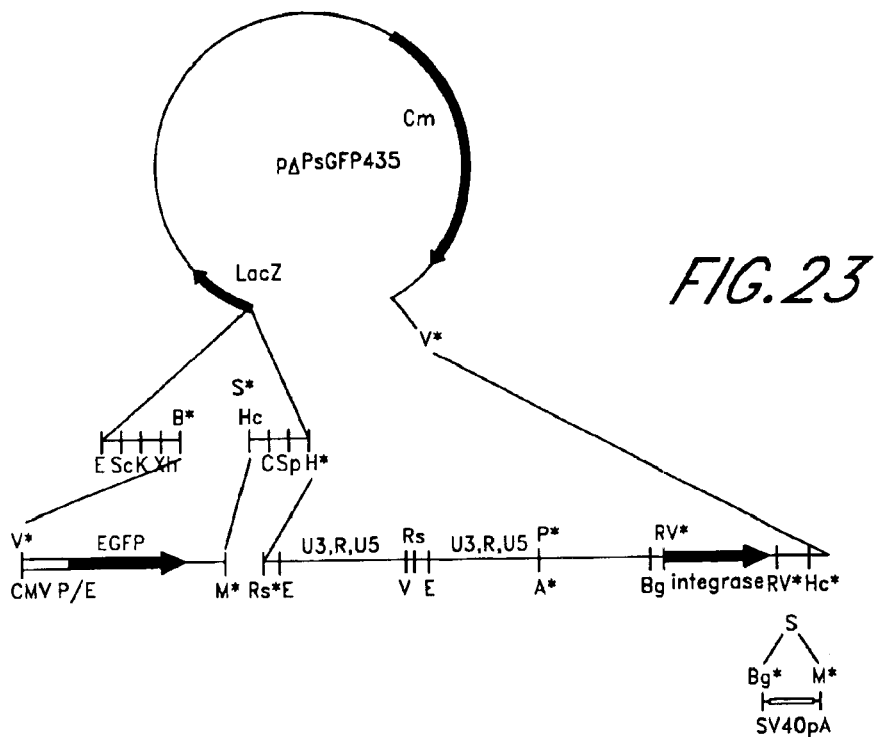
FIG. 23
RESTRICTION ENZYME
A : Apa LI
B : Bam HI
Bg : Bgl II
C : Cla I
E : Eco RI
H : Hind III
Hc : Hinc II
K : Kpn I
M : Mlu I
N : Nhe I
P : Pst I
Rs : Rsa I
RV : Eco RV
S : Sal I
Sc : Sac I
Sp : Sph I
V : Vsp I
Xb : Xba I
X : Xho I

SEQUENCE LISTING

<160> NUMBER OF SEQ ID NOS: 13

<210> SEQ ID NO 1
<211> LENGTH: 31
<212> TYPE: DNA
<213> ORGANISM: Artificial Sequence
<220> FEATURE:
<223> OTHER INFORMATION: Designed PCR primer including 3' region of U3
      and VspI restriction enzyme site to multiply RSV LTR.

<400> SEQUENCE: 1
ggcattaatg tagtcttatg caatactcct g                                          31

<210> SEQ ID NO 2

```
<211> LENGTH: 40
<212> TYPE: DNA
<213> ORGANISM: Artificial Sequence
<220> FEATURE:
<223> OTHER INFORMATION: Designed PCR primer including 5' non coding
      region of p19 gene, HincII, EcoRV and BglII restriction
      enzyme site to multiply RSV LTR and down stream
      region of LTR.

<400> SEQUENCE: 2
gttaacgata tcagatctgc ttgatccacc gggcgaccag                           40

<210> SEQ ID NO 3
<211> LENGTH: 36
<212> TYPE: DNA
<213> ORGANISM: Artificial Sequence
<220> FEATURE:
<223> OTHER INFORMATION: Designed PCR primer including 5' region of RSV
      integrase gene and BamHI restriction enzyme site
      to multiply RSV integrase gene.

<400> SEQUENCE: 3
ttggatccat gcccttgaga gaggctaaag atcttc                              36

<210> SEQ ID NO 4
<211> LENGTH: 33
<212> TYPE: DNA
<213> ORGANISM: Artificial Sequence
<220> FEATURE:
<223> OTHER INFORMATION: Designed PCR primer including 3' region of RSV
      integrase gene, polyA signal to multiply RSV
      integrase gene.

<400> SEQUENCE: 4
tttattttaa ctctcgttgg cagcaagggt gtc                                 33

<210> SEQ ID NO 5
<211> LENGTH: 29
<212> TYPE: DNA
<213> ORGANISM: Artificial Sequence
<220> FEATURE:
<223> OTHER INFORMATION: Designed PCR primer including 5' region of U5
      and VspI restriction enzyme site to multiply RSV LTR.

<400> SEQUENCE: 5
ggcattaatg aagccttctg cttcattca                                      29

<210> SEQ ID NO 6
<211> LENGTH: 51
<212> TYPE: DNA
<213> ORGANISM: Artificial Sequence
<220> FEATURE:
<223> OTHER INFORMATION: Designed PCR primer including 3' region of RSV
      integrase gene, polyA signal, nuclear localization
      signal of SV40 large T antigen to multiply RSV
      integrase gene.

<400> SEQUENCE: 6
tttattttaa accttcctct tcttcttagg actctcgttg gcagcaaggg t              51

<210> SEQ ID NO 7
<211> LENGTH: 858
<212> TYPE: DNA
<213> ORGANISM: Rous sarcoma virus
<220> FEATURE:
<221> NAME/KEY: TATA_signal
<222> LOCATION: (84)...(90)
<220> FEATURE:
<221> NAME/KEY: polyA_signal
```

<222> LOCATION: (107)...(112)
<220> FEATURE:
<221> NAME/KEY: TATA_signal
<222> LOCATION: (431)...(437)
<220> FEATURE:
<221> NAME/KEY: polyA_signal
<222> LOCATION: (454)...(459)
<223> OTHER INFORMATION: A part of circular form of RSV DNA, tandem repeat LTRs and adjacent non coding region.

<400> SEQUENCE: 7

```
acgatcgtgc cttattagga aggcaacaga cgggtctaac acggattgga cgaaccactg      60
aattccgcat tgcggagata ttgtatttaa gtgcctagct cgatacaata aacgccattt     120
taccattcac cacattggtg tgcacctggg ttgatggctg gaccgttgat tccctgacga     180
ctacgagcac atgcatgaag cagaaggctt cattaatgta gtcttatgca atactcctgt     240
agtcttgcaa catgcttatg taacgatgag ttagcaacat gccttacaag gagagaaaag     300
gcaccgtgca cgacgattgg tggaagtaag gtggtatgat cgtaggtacg atcgtgccctt    360
attaggaagg caacagacgg gtctaacacg gattggacga accactgaat tccgcattgc     420
ggagatattg tatttaagtg cctagctcga tacaataaac gccattttac cattcaccac     480
attggtgtgc acctggggttg atggctggac cgttgattcc ctgacgacta cgagcacatg     540
catgaagcag aaggcttcat tggtgaccc cgacgtgatc gttagggaat agtggtcggc     600
cacagacggc gtggcgatcc tgccctcatc cgtctcgctt attcggggag cggacgatga     660
ccctagtaga gggggctgcg gcttaggagg gcagaagctg agtggcgtcg agggagctc      720
tactgcaggg agcccagata ccctaccgag aactcagaga gtcgttggaa gacgggaaga     780
aagcccgacg actgagcggt ccacccccagg cgtgattccg gttgctctgc gtgaccctgg     840
tcgcccggtg gatcaagc                                                   858
```

<210> SEQ ID NO 8
<211> LENGTH: 972
<212> TYPE: DNA
<213> ORGANISM: Rous sarcoma virus
<220> FEATURE:
<221> NAME/KEY: CDS
<222> LOCATION: (1)...(972)
<223> OTHER INFORMATION: precursor integrase or p36 protein
<220> FEATURE:
<221> NAME/KEY: CDS
<222> LOCATION: (1)...(858)
<223> OTHER INFORMATION: mature integrase or p32 protein

<400> SEQUENCE: 8

```
ccc ttg aga gag gct aaa gat ctt cat acc gct ctc cat att gga ccc       48
Pro Leu Arg Glu Ala Lys Asp Leu His Thr Ala Leu His Ile Gly Pro
 1               5                  10                  15 cgc gcg cta tcc aaa gcg tgt aat ata tct atg cag cag gct agg gag       96
Arg Ala Leu Ser Lys Ala Cys Asn Ile Ser Met Gln Gln Ala Arg Glu
             20                  25                  30 gtt gtt cag acc tgc ccg cat tgt aat tca gcc cct gcg ttg gag gcc      144
Val Val Gln Thr Cys Pro His Cys Asn Ser Ala Pro Ala Leu Glu Ala
         35                  40                  45 gga gta aac cct agg ggt ttg gga ccc cta cag ata tgg cag aca gac      192
Gly Val Asn Pro Arg Gly Leu Gly Pro Leu Gln Ile Trp Gln Thr Asp
     50                  55                  60 ttt acg ctt gag cct aga atg gcc ccc cgt tcc tgg ctc gct gtt act      240
Phe Thr Leu Glu Pro Arg Met Ala Pro Arg Ser Trp Leu Ala Val Thr
 65                  70                  75                  80 gtg gac acc gcc tca tca gcg ata gtc gta act cag cat ggc cgt gtc      288
```

-continued

```
                Val Asp Thr Ala Ser Ser Ala Ile Val Val Thr Gln His Gly Arg Val
                             85                  90                  95 aca tcg gtt gct gta caa cat cat tgg gcc acg gct atc gcc gtt ttg       336
Thr Ser Val Ala Val Gln His His Trp Ala Thr Ala Ile Ala Val Leu
            100                 105                 110 gga aga cca aag gcc ata aaa aca gat aac ggg tcc tgc ttc acg tct       384
Gly Arg Pro Lys Ala Ile Lys Thr Asp Asn Gly Ser Cys Phe Thr Ser
        115                 120                 125 aaa tcc acg cga gag tgg ctc gcg aga tgg ggg ata gca cac acc acc       432
Lys Ser Thr Arg Glu Trp Leu Ala Arg Trp Gly Ile Ala His Thr Thr
    130                 135                 140 ggg att ccg ggt aat tcc cag ggt caa gct atg gta gag cgg gcc aac       480
Gly Ile Pro Gly Asn Ser Gln Gly Gln Ala Met Val Glu Arg Ala Asn
145                 150                 155                 160 cgg ctc ctg aaa gat agg atc cgt gtg ctt gcg gag ggg gac ggc ttt       528
Arg Leu Leu Lys Asp Arg Ile Arg Val Leu Ala Glu Gly Asp Gly Phe
                165                 170                 175 atg aaa aga atc ccc acc agc aaa cag ggg gaa cta tta gcc aag gca       576
Met Lys Arg Ile Pro Thr Ser Lys Gln Gly Glu Leu Leu Ala Lys Ala
            180                 185                 190 atg tat gcc ctc aat cac ttt gag cgt ggt gaa aac acg aaa aca ccg       624
Met Tyr Ala Leu Asn His Phe Glu Arg Gly Glu Asn Thr Lys Thr Pro
        195                 200                 205 ata caa aaa cac tgg aga cct acc gtt ctt aca gaa gga ccc ccg gtt       672
Ile Gln Lys His Trp Arg Pro Thr Val Leu Thr Glu Gly Pro Pro Val
    210                 215                 220 aaa ata cga ata gag aca ggg gag tgg gaa aaa gga tgg aac gtg ctg       720
Lys Ile Arg Ile Glu Thr Gly Glu Trp Glu Lys Gly Trp Asn Val Leu
225                 230                 235                 240 gtc tgg gga cga ggt tat gcc gct gtg aaa aac agg gac act gat aag       768
Val Trp Gly Arg Gly Tyr Ala Ala Val Lys Asn Arg Asp Thr Asp Lys
                245                 250                 255 gtt att tgg gta ccc tct cga aaa gtt aaa ccg gac atc acc caa aag       816
Val Ile Trp Val Pro Ser Arg Lys Val Lys Pro Asp Ile Thr Gln Lys
            260                 265                 270 gat gag gtg act aag aaa gat gag gcg agc cct ctt ttt gca ggc att       864
Asp Glu Val Thr Lys Lys Asp Glu Ala Ser Pro Leu Phe Ala Gly Ile
        275                 280                 285 tct gac tgg ata ccc tgg gga gac aag caa gaa gga ctc caa gga gaa       912
Ser Asp Trp Ile Pro Trp Gly Asp Lys Gln Glu Gly Leu Gln Gly Glu
    290                 295                 300 acc gct agc aac aag caa gaa aga ccc gga gaa gac acc ctt gct gcc       960
Thr Ala Ser Asn Lys Gln Glu Arg Pro Gly Glu Asp Thr Leu Ala Ala
305                 310                 315                 320 aac gag agt taa                                                       972
Asn Glu Ser *
```

<210> SEQ ID NO 9
<211> LENGTH: 21
<212> TYPE: DNA
<213> ORGANISM: Artificial Sequence
<220> FEATURE:
<223> OTHER INFORMATION: Designed PCR primer including 5' region of GFP
      gene and a part ofNheI restriction enzyme site to
      multiply GFP gene.

<400> SEQUENCE: 9
ctagcgctac cggtcgccac c                                               21

<210> SEQ ID NO 10
<211> LENGTH: 20

```
<212> TYPE: DNA
<213> ORGANISM: Artificial Sequence
<220> FEATURE:
<223> OTHER INFORMATION: Designed PCR primer including antisense
      sequence of GFP ORF to multiply a part of GFP gene.

<400> SEQUENCE: 10
gttgccgtcc tccttgaagt                                            20

<210> SEQ ID NO 11
<211> LENGTH: 21
<212> TYPE: DNA
<213> ORGANISM: Artificial Sequence
<220> FEATURE:
<223> OTHER INFORMATION: Designed PCR primer including U5 region LTR
      sequence to
      multiply a part of integrated plasmid vecter.

<400> SEQUENCE: 11
ttggtgtgca cctgggttga t                                          21

<210> SEQ ID NO 12
<211> LENGTH: 36
<212> TYPE: DNA
<213> ORGANISM: Artificial Sequence
<220> FEATURE:
<223> OTHER INFORMATION: Designed PCR primer including 5' end of GFP ORF
      sequence to multiply a part of GFP gene.

<400> SEQUENCE: 12
atggtgagca agggcgagga gctgttcacc ggggtg                          36

<210> SEQ ID NO 13
<211> LENGTH: 20
<212> TYPE: DNA
<213> ORGANISM: Artificial Sequence
<220> FEATURE:
<223> OTHER INFORMATION: Designed PCR primer including a part of GFP ORF
      sequence to multiply a part of GFP gene.

<400> SEQUENCE: 13
gtcgagctgg acggcgacgt                                            20
```

PLASMID VECTOR COMPRISING A RETROVIRAL INTEGRASE GENE AND AN INTEGRASE RECOGNITION REGION

TECHNICAL FIELD

The present invention relates to plasmid vectors capable of integrating any DNA of interest into the host cell genome.

The present invention further relates to methods for producing transformants and transgenic animals (which may be referred to as "TG animals," hereinafter), and to methods for producing useful substances using such plasmid vectors.

BACKGROUND ART (1) Applications of Techniques to Introduce Foreign DNA

Inserting foreign DNA into the host cell genome is a technique of significant importance that finds wide applications in many industries and medical fields.

One principal application includes the production of useful substances. In the early stage, vectors employing *Escherichia coli* as host cells were constructed for this purpose. These vectors are still in use today. A drawback with such system is that the produced proteins are modified in a different manner from the system of mammals or birds. This presents a problem when it is desired to produce and utilize useful proteins of humans or other animals. In particular, *Escherichia coli* is not ideal for producing glycoproteins since the addition of sugar chains to proteins does not take place in the *E. coli* system. Also, the resulting proteins often form insoluble aggregates in *E. coli*, which may require further treatment in order to obtain physiologically active proteins.

To avoid this problem, vectors employing yeast as hosts are used. Unlike *E. coli*, the addition of sugar chains occurs in yeast. However, since different types of sugar chains are added in yeast, problems may arise in terms of physiological activities. The produced proteins in yeast also tend to form aggregates as in *E. coli*.

A method using viruses as an expression vector is also widely used. At present, an expression system employing baculoviruses as a vector is widely used for the purpose of obtaining physiologically active proteins in large quantities. In this system, it is more likely that physiologically active proteins are obtained as compared to the other two systems described above. In this case, however, the problem of different-type sugar chains added to glycoproteins and the problem of the formation of protein aggregates still remain. Further, the amount of a protein to be expressed may vary widely depending on the type of the protein to be produced. Thus, it is presently difficult to estimate the amount of a protein to be expressed until recombinants are constructed and the protein has actually been expressed.

In another method, plasmid vectors are introduced into animal cells to express useful proteins. This approach has an advantage that little problem arises regarding the modification of expressed proteins. Various techniques are available to introduce plasmid vectors into cells, including electroporation, calcium phosphate-DNA transfection, and the use of liposome. However, in general, the DNA introduced into cells using these techniques is not inserted into the genome and is thus lost and eventually eliminated as the cells grow. Thus, each production of a protein requires the introduction of the DNA.

When plasmid DNA is introduced into cells, recombination may occur between the plasmid DNA and the genome of the host cell, resulting in the integration of the plasmid DNA into the genome, though the frequency of the occurrence is extremely low. In general, once integrated into the genome of the host cell, the DNA will not be lost through the proliferation of the host cells. Thus, cells that can permanently express a protein of interest can be obtained by selecting the cells that the vector DNA encoding the protein has been integrated into their genome. The selection is made possible by applying an antibiotic to select the cells that are expressing a foreign gene along with a protein resistant to the antibiotic. Hence, the cells capable of expressing useful proteins are obtained selectively. However, the protein of interest is generally expressed in small amounts in the cells obtained in this manner, limiting the range of application of the method.

Production of useful proteins by the use animals has also been attempted. For this purpose, a method is attempted in which useful proteins are expressed in milk of cows, goats, hogs or the like. In another approach, useful proteins are expressed in eggs of chickens. These methods, when successfully carried out, make it possible to obtain useful proteins in substantial amounts. However, it is disadvantageous that, in the former approach, costs needed to establish transgenic (TG) animals using large mammals such as cows, goats and hogs tend to be enormous.

In the latter approach making use of chickens, it will be convenient if foreign DNA can be introduced into laid eggs as they are easy to handle. In producing mammalian TG animals, DNA is injected into nuclei of fertilized eggs using a micromanipulator before cell division is started or at a very early stage after cell division is started. This is not applicable, however, to already laid chicken eggs since cell division has already proceeded to a significant degree when the eggs are laid. Also, it is extremely complicate to introduce foreign genes into each of cells that have multiplied in number through cell division using a micromanipulator. In a recent report, fertilized eggs were collected from chickens before they underwent cell division, and plasmid DNA was microinjected into the eggs. The eggs were then artificially incubated until hatching by extrasomatic incubation. The report describes that the introduced foreign genes were successively transferred to the successive generations (Love, J., et al., *Biotechnology*, 12, 60–63, 1994). This approach still requires special techniques such as micromanipulation and extrasomatic incubation of fertilized chicken eggs. To overcome these problems, a method is proposed in which a foreign gene is introduced into primordial germ cells which are collected from chick embryos at an early developmental stage, and the cells are returned to early embryos in other developing chicken eggs which are then hatched. In this method, chicks whose germline cells have contained a foreign gene are obtained. When these chicks are grown and allowed to reproduce, it is expected that the foreign gene is transmitted to the descendants. However, the method has not yet been put to practical use because no effective way has been established so far to efficiently insert a foreign gene into the genome of the collected primordial germ cells.

In recent years, an approach using cloning technologies has been developed. In this approach, a gene is introduced into somatic cells collected from an animal in vitro, and the cells having genome into which the foreign gene has been integrated are selected. Using the micromanipulation technique, the nuclei collected from the selected cells are implanted into ova that have had their own nuclei removed in advance. The ova are then returned to the uterus of the female animal to obtain progeny. However, the implantation of nuclei into cells using, for example, micromanipulation technique requires special skills and, moreover, enormous costs will be needed to establish cloned animals.

Injection of DNA using a micromanipulator is also a key technique in introducing foreign DNA into primordial germ cells of chickens. However, since as many as one hundred primordial germ cells need to be returned to one early embryo in a developing chicken egg, the method using a micromanipulator is not ideal for handling the numerous primordial germ cells.

Methods for handling numerous primordial germ cells include introducing plasmid DNA by means of electroporation and using retrovirus vectors as an inherently infectious vector. In the former method, it has been reported that a gene can be introduced into primordial germ cells with a relatively high efficiency by using electroporation (Hong, Y. H., et al., *Transgenic Res.*, 7, 247–252, 1998). However, it is still uncertain whether the gene introduced is transmitted to offspring in a stable manner since the method employs ordinary plasmid vectors. Depending on a report as to the latter case of retrovirus vectors, when the primordial germ cells into which a foreign gene has been introduced using retroviral vectors are implanted in embryos of other eggs, the foreign gene is transferred to offspring of the chickens developed from the embryos (Vick, L., et al., *Proc. R. Soc. Lond. B. Biol. Sci.*, 251, 179–182, 1993). The method, however, is disadvantageous in that it takes a considerable amount of time to construct such vectors and in that the viruses generally do not replicate efficiently enough and viral infection is typically inefficient. Also, it is difficult to construct retrovirus vectors with a strong promoter.

While TG animals have been described in regard to the production of useful proteins, they are used in various other applications. TG mice, for example, are used to analyze functions of certain genes. TG mice into which a gene encoding a receptor for a particular pathogen has been introduced are used as a model animal for the disease caused by the pathogen. One application of TG animals includes producing animals for providing organs for organ transplantation.

Although making TG mice is an already established technique, it requires a special skill, i.e., micromanipulation, and associated equipment.

Recently, a method for producing TG animals in a more convenient manner has been proposed wherein DNA is injected directly into testis of male animals, and the males are allowed to naturally mate with female animals to introduce the foreign gene into fertilized eggs. Expression of foreign gene has been observed in early blastcysts developed from fertilized eggs which are obtained by injecting DNA into testes of male mice and allowing them to naturally mate(Ogawa S., et al., *J. Reproduction and Development*, 41, 379–382, 1995). However, the foreign gene introduced in this manner may not be passed on to the progeny in a stable fashion and thus the method is not effective enough to ensure the production of TG mice.

The idea of DNA vaccine has been developed recently, and significant efforts have been put into developing this concept. The principle of DNA vaccine is that immunity can be elicited in animals following the administration of DNA encoding a certain antigen under the control of promoter by injection or by particle bombardment. The basis of this idea is that DNA is more convenient to handle and is thus more advantageous in developing a new vaccine as compared to attenuated or inactivated pathogens used as vaccines, or peptides that induce protective immunity. Expression of foreign genes has actually been observed in cells of animals inoculated with plasmid DNA. Humoral immunity, as well as cellular immunity which typically is difficult to induce by inactivated vaccines, has been induced in these animals (Ulmer, J. B. et al., *Science*, 259, 1745–1749, 1993). However, DNA vaccines have not been put to practical use hitherto since the induction of immune responses requires significant amounts of DNA. One reason for this is that the DNA taken up by cells might be eliminated in a short period of time. To cope with this, it is investigated to utilize retroviruses, which become a provirus, as a vector. In particular, it is proposed to use as a vaccine a vector into which env/rev genes of HIV, a virus responsible for AIDS, have been incorporated (Irwin, M. J., et al., *J. Virol.*, 68, 5036–5044, 1994). The use of retroviruses as a vector is accompanied by several problems, however. (This will be described in detail later.)

Techniques for integration of a foreign gene into the genome of host cells are used as a gene therapy to treat incurable diseases of humans. A primary application of the gene therapy concerns treating genetic diseases. Genetic diseases are defined as the diseases caused by defects or mutation in some important genes. Thus, by introducing normal genes that compensate for the defective or mutated genes, the symptoms may be ameliorated or eliminated. Although the number of genetic diseases to which the gene therapy can be applied is limited as it is literally impossible to introduce a gene into all of the cells, the gene therapy has proven to be successful in treating some genetic diseases including adenosine deaminase (ADA) deficiency.

A second application of the gene therapy concerns treating cancers as described below. A tumor suppressor gene or a gene that expresses antisense RNA of an oncogene is introduced to suppress the development of cancers. This approach is thought to be one of the most promising applications of the therapy. In another approach, a gene encoding a cytokine is introduced into immunocompetent cells or cancer cells, or a gene associated with a major histocompatibility complex (MHC) is introduced into cancer cells in order to enhance immune activities of host and consequently suppress cancers. Also, a gene that makes cells resistant to anticancer drugs may be introduced to protect the cells, such as bone marrow stem cells, that are otherwise susceptible to the anticancer drugs. This intends to enable administration of anticancer drugs in larger dosages.

A third application of the gene therapy concerns treating infectious diseases. The diseases addressed by this approach include AIDS and hepatitis C where pathogens relatively grow slowly and evade the immune system of the hosts. A gene capable of suppressing the expression of the genes that are essential to the growth of a pathogen (e.g., a gene encoding antisense RNA or a gene encoding a ribozyme that specifically cleaves viral RNA) may also be introduced into the target cells of the pathogen, such that the cells that have contained the gene will be protected against the pathogens. As such, the concept of intracellular immunization, meaning anti-disease activity on a cell basis, has recently been proposed and much effort has been made to develop the idea (Baltimore, D., *Nature*, 335, 395–396, 1988).

(2) Methods for Inserting DNA Using Retrovirus Vectors or the Like.

A method for inserting foreign DNA into a genome involves introducing a plasmid vector having a foreign DNA and a drug resistant gene into cells, and then, by using the drug, selecting the cells into the genome of which the foreign DNA has been incorporated. While this method is effective to a certain degree, its use is limited to certain applications such as cultured cells due to extremely low efficiencies.

Another method for inserting foreign DNA into the genome, which is often used to produce TG animals, involves directly injecting an amount of DNA into nuclei. This method achieves a higher probability that the foreign DNA is integrated into the genome since a large quantity of foreign DNA is directly injected into nuclei. The method, however, is not ideal for handling a number of cells at a time because it requires special equipment such as a micromanipulator as well as skills to use such equipment and because cells have to be handled individually, making the method extremely difficult.

Accordingly, the most popular method for inserting any DNA sequence of interest into the genome of host cells, at present, seems to be the one employing retroviruses. Retroviruses are single-stranded RNA viruses, and their genomic RNA has the structure of which type is essentially a messenger RNA (mRNA) that has a cap structure at 5' end and a poly-A tail at 3' end. Upon infection, viral particles bind to receptors of the host cell via a specific binding. The virus envelope and the cell membrane fuses to release a pre-integration complex into the cytoplasm. The complex includes reverse transcriptase and integrase, each originating from the viral particle, in addition to viral RNA. The reverse transcriptase catalyzes the synthesis of a double-stranded, linear DNA using the viral RNA as a template. Through this process, a long repetitive sequence, termed the long terminal repeat(LTR), which is not found in the viral RNA, is formed at each end of the DNA strand. This double-stranded linear DNA, together with integrase, forms a complex and moves into a nucleus where it subsequently circularizes. The resulting circular DNA is integrated into the genome of the host cell with the help of integrase (*Molecular Biology of Genes*, 4th ed. Watson, J. D., Hopkins, N. H., Roberts, J. W., Steitz, J. A., Weiner, A. M., Japanese translation prepared by Kenichi Matsubara, Keiko Nakamura, Kinichiro Miura, published by Toppan Ltd., 1988). However, there is a report suggesting that the precursor of the integration into the host genome is not the circular DNA but linear double stranded DNA (Brown, P. O., et al., *Proc. Natl. Acad. Sci. USA.*, 86, 2525–2529, 1989). It is thought that the integrase that plays a role here is not newly produced from the viral genome via transcription and translation of the genome following the infection. Rather, the enzyme seems to be of virion-origin and is thought to be brought into the host cell upon infection. The localization of integrase into a nucleus and functioning of the enzyme appear to be occurring while integrase is bound to the viral genome.

A report suggests that the integration into the genome of host cells occurs at a site where LTRs at each end of the linear double-stranded DNA are joined to one another as the linear double-stranded DNA circularizes (Panganiban, A. T, and Temin, H. M., *Cell*, 36, 673–679, 1984). Panganiban, A. T, and Temin, H. M. (*Nature*, 306, 155–160. 1983) and Duyk, G. et al. (*J. Virol.*, 56, 589–599, 1985) describe the recognition sequences of integrase.

The form of virus that is integrated into the genome of a host cell is referred to, as a provirus. RNA polymerase II of the host cell recognizes a promoter in the LTR of a provirus, initiating the transcription of the retroviral genome into RNA. A part of the transcribed RNA serves as viral RNA while the other part of the RNA undergoes splicing and serves as mRNA to synthesize viral proteins. As described above, retroviruses are integrated into the genome of host cells and become a provirus in their life cycle. This characteristic makes retroviruses a vector for inserting a foreign gene into the genome of host cells.

Retroviruses carry the genes gag, pol, and env. When these genes are defective, the retroviruses can still infect the host cell but are no longer capable of producing virions of the next generation. This implies the possibility that a retrovirus, in which one or more of these genes have been made defective and a foreign gene has been inserted instead, may be used as a safe vector that can insert a foreign gene into the genome of the host cell but will no longer produce infectious virions.

However, a problem exists concerning the safety of the retroviral vectors. In order to enable these vectors to replicate, cells expressing the viral proteins for the defective genes (i.e., helper cells) are established and used. Thus, there is a chance, though small, that a homologous recombination occurs between the viral genes present in the helper cell and the vector plasmid carrying a foreign gene, resulting in replicant competent retroviruses (RCRs) that have regained the ability to replicate. In fact, there is a report in which these viruses have caused the T-cell lymphoma in monkeys (Donahue, R. E., et al., *J. Exp. Med.*, 176, 1125–1135, 1992).

While retroviral vectors are, in principle, ideal for inserting a foreign gene into the genome of host cells, some drawbacks exist with this approach such as follows:

(i) It is difficult to obtain high-titer viruses. The highest titer of the viruses that can be obtained is typically around $10^5$ to $10^7$ colony forming unit (cfu)/ml.

Also, polypeptides such as SU polypeptides constituting envelope proteins that is involved in the specific binding to the receptors of the host cell will be lost during the process of concentration of virions, for example, by centrifugation. Thus, it is difficult to obtain infectious viral particles in high concentrations. This is one of the reasons for the difficulty in obtaining high-titer viruses.

(ii) The efficiency of viral infection is low. This, in addition to the difficulty in obtaining high-titer viruses, also makes it difficult to achieve the gene introduction with sufficient efficiency.

(iii) It is difficult to construct recombinants incorporating a strong promoter. This is a problem when high levels of foreign gene expression are desired.

(iv) Generally, it takes considerable amount of time to establish practical viral vectors.

(v) In many cases, the infection efficiency of retroviral vectors and the expression efficiency of the introduced gene are low.

(vi) Viruses tend to be inactivated by complements in vivo.

Advantages and disadvantages of the vectors for introducing a gene that are currently in use are summarized in Table 1 below.

TABLE 1

Comparison between vectors for gene introduction

| | Advantages | Disadvantages |
|---|---|---|
| RETROVIRAL VECTORS | * They are integrated into the genome of host cells.<br>* They can be used to introduce a gene into various types of cells including blood cells.<br>* They can be readily constructed by using helper cells[1]. | * Insertion of the vector may cause mutation in the gene of the host cells[2].<br>* When viruses belonging to the oncovirus subfamily are used as a vector, they cannot use for gene transfer into non-dividing cells.<br>* Low expression efficiency of introduced gene (Constructing viral vectors with a strong promoter is difficult).<br>* It is difficult to obtain high-titer viruses.<br>* Infectious viruses may arise as a result of homologous recombination[3]. |

TABLE 1-continued

Comparison between vectors for gene introduction

|  | Advantages | Disadvantages |
|---|---|---|
| ADENO-VIRAL VECTORS | * They can transfer a foreign gene with high efficiency.<br>* They may be used for gene transfer in vivo.<br>* They may be used for gene transfer into non-dividing cells.<br>* High-titer vectors can be prepared. | * They are not inserted into host genome, and expression of introduced foreign gene is transient.<br>* They exhibit strong antigenicity and thus are not suitable for repeated administration to living organisms.<br>* Constructing vectors involves complicated process.<br>* They exhibit cytotoxicity. |
| ADENO-ASSOCIATED VIRAL VECTORS | * They can transfer a foreign gene into dividing and non-dividing cells with relatively high efficiency.<br>* They are integrated into host genome, though efficiency is not always high.<br>* They do not exhibit pathogenicity or cytotoxicity. | * Site-specific integration, which is observed in wild type viruses, does not occur.<br>* Genes equal to or larger than 4.5 kb in size can not be inserted into vectors.<br>* Construction of vectors involves complicated process.<br>* Mass-production of the vectors is difficult.<br>* Low titer |

[1]Cells carrying plasmids that encode viral proteins but do not have a packaging signal.
[2]With regard to the possibility of the transformation into cancer, which is of particular concern, the chance of occurrence seems to be very small due to the involvement of several genes in the transformation. No case of cancer development caused by retroviral vectors has ever been reported.
[3]Occurrence of T-lymphoma was reported in monkeys in 1991.

Among reports concerning integrase of retroviruses is the one by Tanaka et al (Shoji-Tanaka, A., et al., *Biochem. Biophys. Res. Commun.*, 203, 1756–1764, 1994). In this report, it is observed that the efficiency of DNA introduction into cells was increased by several times by introducing into cells purified integrase of bovine leukemia viruses. The integrase was expressed in *E. coli* and purified. Using liposome carriers, the purified integrase was introduced along with plasmids incorporating an integrase recognition site. The degree of this increase in the efficiency of DNA introduction into cells was varied depending on whether or not a linking site of LTRs and sequences adjacent to the linking site were contained in the plasmid. Determination of cleavage sites in the plasmid DNA integrated into the genome using the southern hybridization technique indicated that integration occured at the site where the LTR linking site exists when the plasmids were introduced into cells with integrase, whereas recombination seems to have occurred in the plasmid in the regions other than that which includes the LTR linking site when plasmids alone were introduced into cells without integrase.

In this report, the integrase was first mixed with the DNA, and the mixture was then incubated at a room temperature for thirty minutes. This is supposed to facilitate the formation of complexes of integrase and the DNA by utilizing integrase's ability to bind to DNA. Thus, following the introduction into cells by means of liposome carriers, the integrase and the plasmid are not transferred into a nucleus individually, but they are transferred into a nucleus as a complex. Accordingly, the insertion of DNA into the genome is carried out in this system by making use of the life cycle of retroviruses described above.

However, Mochii reports that no increase was observed in the efficiency with which a foreign gene was integrated into the genome of cells when the above-described method by Tanaka et al was applied to fertilized eggs of chickens (*Protein, Nucleic acid and Enzyme*, 40, 2265–2273, 1995).

DISCLOSURE OF THE INVENTION

Accordingly, it is an object of the present invention to provide a vector capable of integrating foreign DNA into the genome of a host cell. Requirements for the vector include the following: it should be easy to construct the vector with an incorporated foreign gene; the vector should be mass-produced easily; the integration of a foreign DNA into the genome must take place efficiently; and the safety of the vector must be high. The present invention is directed to develop a vector which meets these requirements.

Another object of the present invention is to provide a transformant, a TG animal and the like which make use of the above-described vector, and a production method thereof as well as a method for producing useful substances.

To achieve these objects, the present inventors have attempted to construct a vector which has overcome the above-described problems while exploiting the advantages of retroviruses. An advantage of retroviral vectors that are commonly in use today is that DNA of interest can be integrated into the genome of host cells by making use of the life cycle of retroviruses, whereas the drawback primarily concerns the difficulty in handling retroviruses.

During the course of study, the present inventors have conceived of the idea of producing a plasmid vector which contains an integrase gene and an integrase recognition site. Manipulation procedures are well established for plasmids. Surprisingly, it has turned out that such plasmids are capable of integrating foreign DNA into the genome of host cells with great efficiency. This discovery ultimately led to the present invention.

Thus, the present invention is a plasmid vector comprising:

(D1) an integrase gene;

(D2) a segment of DNA forming a region for controlling the expression of the integrase gene; and (D3) a segment of DNA serving as an integrase recognition region when integrase catalyzes the integration reaction. The vector may be referred to as a plasmid vector containing (D1) through (D3) hereinbelow.

Also, the present invention is a plasmid vector comprising:

(D1) an integrase gene;

(D2) a segment of DNA forming a region for controlling the expression of the integrase gene;

(D3) a segment of DNA serving as an integrase recognition region when integrase catalyzes the integration reaction; and (D4) any DNA to be integrated into the genome of host cells. The vector may be referred to as a plasmid vector containing (D1) through (D4) hereinbelow.

Also, the present invention includes the plasmid vector in which the DNA segment (D3) at least includes a connecting sequence of terminal bases formed when one LTR is joined to the other LTR.

Also, the present invention includes the plasmid vector which includes a region formed by two LTRs joined together, and both of the DNA segments (D2) and (D3) are situated within the region formed by the two LTRs joined together.

Also, the present invention includes the plasmid vector, wherein a DNA segment encoding a nuclear localization signal is further added to the integrase gene.

Also, the present invention includes the plasmid vector, wherein the integrase gene and/or the LTRs are derived from viruses belonging to Retroviridae.

Also, the present invention include the plasmid vector, wherein the viruses belonging to Retroviridae include viruses belonging to subfamily Oncovirinae of Retroviridae.

Also, the present invention includes a transformant transformed by using the plasmid vector.

Also, the present invention includes a chimeric animal other than humans, in which the plasmid vector has been integrated into the genome thereof.

Also, the present invention includes a transgenic animal other than humans, in which the plasmid vector has been integrated into the genome thereof.

Also, the present invention includes a method for producing a bird that has incorporated foreign DNA. The method includes injecting the plasmid vector having the components (D1) through (D4) into an embryo in an egg of a bird; allowing the DNA segment (D4) to integrate into the genome of cells that constitute the embryo; and hatching the egg to obtain an individual that has incorporated the DNA segment (D4).

Also, the present invention includes another method for producing a bird that has incorporated foreign DNA. The method includes introducing the plasmid vector having the components (D1) through (D4) into primordial germ cells collected from a bird embryo at an early developmental stage; allowing the DNA segment (D4) of the plasmid vector to integrate into the genome of the primordial germ cells; injecting the primordial germ cells that have incorporated the DNA segment (D4) into an early embryo in an egg laid by other individuals; and hatching the egg to obtain an individual that has incorporated the DNA segment (D4).

Also, the present invention includes a method for producing a transgenic bird, in which the individual which is obtained in the method for producing a bird that has incorporated foreign DNA and whose germline cells have incorporated foreign DNA is allowed to naturally mate or artificially fertilized.

Also, the present invention includes a method for producing a transgenic animal, in which the plasmid vector having the components (D1) through (D4) is injected into a testis of a male non-human vertebrate animal, and the animal having the plasmid vector injected thereinto is allowed to naturally mate or artificially fertilized.

Also, the present invention includes a method for producing a useful substance. The method includes providing the plasmid vector having the components (D1) through (D4), wherein the DNA segment (D4) of the plasmid vector includes a region encoding a protein and a control region for controlling the expression of the protein; introducing the plasmid vector into a host cell; and allowing the DNA segment (D4) to integrate into genome of the host cell such that the protein encoded by the DNA segment (D4) is expressed in the host cell to produce the useful product.

Also, the present invention includes another method for producing a useful substance. The method includes providing the plasmid vector having the components (D1) through (D4), wherein the DNA segment (D4) of the plasmid vector includes a region encoding a protein and a control region for controlling the expression of the protein; injecting the plasmid vector into a bird embryo; and allowing the DNA segment to integrate into the genome of cells that constitute the embryo to produce a bird that has incorporated the DNA segment in somatic cells such that the useful substance is produced in an egg laid by the bird that has incorporated the DNA segment.

Also, the present invention includes another method for producing a useful substance. The method includes providing the plasmid vector having the components (D1) through (D4), wherein the DNA segment (D4) of the plasmid vector includes a region encoding a protein and a control region for controlling the expression of the protein; injecting the plasmid vector into an embryo in an egg of a bird; allowing the DNA segment to integrate into the genome of cells that constitute the embryo to produce a bird that has incorporated the DNA segment; hatching the egg to obtain a first generation bird whose germline cells have incorporated the DNA segment; obtaining the useful substance in eggs laid by birds selected from the group consisting of a transgenic bird heterozygous with respect to the DNA segment produced by allowing the first generation birds to naturally mate or artificially fertilizing the first generation birds; a transgenic bird heterozygous or homozygous with respect to the DNA segment produced by allowing the heterozygous transgenic birds to mate or artificially fertilizing the heterozygous transgenic birds; and a transgenic bird heterozygous or homozygous with respect to the DNA segment produced by continuing to cross the heterozygotic or homozygotic transgenic birds through successive generations.

Also, the present invention includes another method for producing a useful substance. The method includes providing the plasmid vector having the components (D1) through (D4), wherein the DNA segment (D4) of the plasmid vector includes a region encoding a protein and a control region for controlling the expression of the protein; introducing the plasmid vector into primordial germ cells collected from a bird embryo at an early developmental stage; allowing the DNA segment of the plasmid vector to integrate into the genome of the primordial germ cells; injecting the primordial germ cells that have incorporated the DNA segment into an early embryo in an egg laid by other individuals; hatching the egg to obtain a first generation bird whose germline cells have incorporated the DNA segment; obtaining the useful substance in eggs laid by birds selected from the group consisting of a transgenic bird heterozygous with respect to the DNA segment produced by allowing the first generation birds to naturally mate or artificially fertilizing the first generation birds; a transgenic bird heterozygous or homozygous with respect to the DNA segment produced by allowing the heterozygous transgenic birds to naturally mate or artificially fertilizing the heterozygous transgenic birds; and a transgenic bird heterozygous or homozygous with respect to the DNA segment produced by continuing to cross the heterozygotic or homozygotic transgenic birds through successive generations.

As used herein, the term "introduction of a gene" refers to introduction of a gene into cells, and the term "integration of a gene" refers to incorporation of a gene into the genome of cells. However, when the term "introduction" is used in the context of transgenic (TG) animals, it means "integration." In this specification, animals into which a gene has introduced may be referred to as "TG animals."

The term "integrase gene" as used herein, refers to a segment of DNA encoding a protein called integrase. As used herein, the term "genome" refers to nucleic acids which constitute the genome.

Without wishing to be bound by a theory, the mechanism that allows for the efficient integration of DNA of interest into the genome of host cells is believed to be as follows, though it has not been fully understood yet. Once introduced into cells, the vectors of the present invention, like other ordinary vectors, move into a nucleus where the integrase gene on the vector is transcribed into mRNA, which in turn is transported to the outside of the nucleus into the cytoplasm where it is used to synthesize integrase in ribosomes. The synthesized integrase is again internalized into the nucleus with the help of something such as the nuclear localization signal or the like. Inside the nucleus, the integrase recognizes the recognition region incorporated in the vector of the present invention which serves as a recognition site for integrase when the integrase catalyzes the integration reaction. It is in this region that the integrase cleaves the vector and inserts it into the genome of host cells. It is thought that, through these processes, the vectors of the present invention can insert any DNA to be integrated into the genome of host cells.

When retroviruses infect cells, the integration of viral genome into the host genome is mediated by integrase brought in by the infecting virions. Hence, it appears that the integrase moves along with the viral genome. In contrast, the vector of the present invention employs a unique pathway that is not seen in the lifecycle of retroviruses. In accordance with the vectors of the present invention, an integrase gene carried by a plasmid is expressed in the host cell, and the resulting integrase mediates the integration of the plasmid into the host genome. The idea is of significant novelty in that an integrase gene incorporated in a vector is expressed in host cells to synthesize integrase, and this integrase, synthesized in the host cell, recognizes an base sequence region which is made based on the LTRs and is pre-incorporated into the plasmid vector so as to mediate the integration of the circular DNA into the genome.

The present invention presents novel plasmid vectors. A wide variety of applications are contemplated for the novel plasmid vectors in accordance with the present invention. Embodiments of the present invention will be described based on three general categories: (1) plasmid vectors and transformants; (2) TG animals and production methods thereof; and (3) other applications of the present invention.

(1) Vectors and Transformants in Accordance with the Present Invention.

In one aspect, the present invention provides a plasmid vector containing:

(D1) an integrase gene;

(D2) a segment of DNA forming a region for controlling the expression of the integrase gene; and (D3) a segment of DNA serving as an integrase recognition region when integrase catalyzes the integration reaction.

The vectors in accordance with the present invention are integrated into the genome of host cells with great efficiency. Thus, any desired DNA can be inserted into the genome of a host cell by incorporating any DNA of interest into the vector containing (D1) through (D3) using ordinary methods, and introducing the vector into the host cell.

In another aspect, the present invention provides a plasmid vector containing:

(D1) an integrase gene;

(D2) a segment of DNA forming a region for controlling the expression of the integrase gene;

(D3) a segment of DNA serving as an integrase recognition region when integrase catalyzes the integration reaction; and (D4) any DNA to be integrated into the genome of host cells.

The vector of the present invention can be prepared by incorporating the DNA components (D1), (D2), and (D3) into a plasmid. Plasmids into which the components (D1), (D2), and (D3) are to be incorporated are selected based on factors such as the size of the DNA to be integrated into the genome of a host cell and the easiness of handling. A known plasmid for which a restriction map has already been established may be used as such plasmids. Among known plasmids which may be used are, for example those of pUC series, pBR series, and pACYC series.

First, the component (D1) will be described. Generally, integrase, a protein produced in the cells infected with a retrovirus, catalyzes the reaction by which a viral genome replicated by reverse transcriptase in a host cell is incorporated into the host chromosome (*Dictionary of cellular and molecular biology*. 1st ed. Tokyo Kagaku Dojin). Integrase genes, i.e., DNA sequences encoding integrase, are described in journals such as *Nucleic Acids Res.*, 18 4022, 1990., *Virolog*, 137 358–370, 1984., and *Cell*, 32 853–869, 1983. These known integrase genes may be used in the vectors of the present invention. Alternatively, an integrase gene may be obtained, for example, by constructing an appropriate primer based on a known DNA sequence and performing PCR (polymerase chain reaction), and the thus obtained integrase gene may be used.

An integrase protein exists as 36 kDa and 32 kDa proteins in a virion though it is synthesized as a 36 kDa protein. This implies that the 36 kDa protein is a precursor of the 32 kDa protein. It has been observed that each of the 36 kDa and 32 kDa proteins has integrase activity (Terry, R., et al., *J. Virol.*, 62, 2358–2365, 1988). Thus, a gene encoding either of the two proteins can be used as the integrase gene.

Next, the component (D2) will be described. The plasmid vector of the present invention includes a segment of DNA forming an expression control region that allows the expression of the integrase gene incorporated in the plasmid vector in host cells. DNA segments commonly used for controlling the gene expression including a promoter, an enhancer, a silencer or the like may be provided in the expression control region. Expression control regions for the integrase gene inherent in retroviruses may be used as the expression control region. In addition to those derived from retroviruses, any control region that can promote the expression of an integrase gene in host cells may be used and properly selected depending on the type of host cells and the like. For example, when the expression of integrase gene is desired irrespective of the type of cells, a promoter in the LTR of retroviruses or a promoter of SV40 may be used. In contrast, the integrase gene may be expressed in a specific type of cells when it is desired. This is achieved by selecting the expression control region depending on the type of the cells. For example, the expression control region of the myosin β-heavy chain may be used for muscle cells. For liver cells, the expression control region of albumin or α-fetoprotein may be used. For B-lymphocytes, the expression control region of immunoglobulin may be used. Also, when the cell-specific expression of the integrase gene is desired in cancer cells, a promoter for carcinoembryonic antigen or promoters for c-erb B2, B3, or B4 may be used.

Next, the component (D3) will be described. The plasmid vector of the present invention also contains a segment of DNA that serves as a recognition region recognized by integrase when integrase catalyzes the integration reaction (which may be referred to as an integrase recognition region throughout this specification). The integrase recognition region at least contains a region which is recognized by integrase as its substrate when integrase catalyzes the integration reaction, in which integrase inserts a circular DNA into the genome of host cells.

One example of the integrase recognition region is a segment of DNA containing at least a connecting sequence of terminal bases which is formed of the terminal base in one LTR and the terminal base in the other LTR(linking site), when one LTR is joined to the other. The sequence of about eight-base pairs long including the linking site and bases on either side thereof is sometimes referred to as the attachment (att) sequence. Examples of the attachment sequences include the "CATTAATG" sequence which has been reported in RSV (*Proc. Nat. Acad. Sci. USA.*, 78, 4299–4303, 1981), Murine leukemia virus (*Cell*, 63, 87–95, 1990), Rous associated virus 2 (*J. Virol.*, 56, 589–599), Spleen necrosis virus (*Cell*, 36, 673–679, 1984) and in Avian reticuloendotheliosis virus (*Cell*, 36, 673–679, 1984), the "CAGTACTG" sequence reported in HIV (*J. Virol.*, 68, 3558–3569, 1994), or the "CAGCACTG" sequence reported in Visna virus (*J. Virol.*, 68, 3558–3569, 1994).

The LTRs (long terminal repeats) are long terminal repeated sequences residing at both end of viral DNA of retroviruses. In general, an LTR is a segment of DNA consisting of U3-R-U5 sequences. The linking site or the attachment sequence described above is formed when the two LTR terminals are "U5-U3" and "U3-U5," respectively. Thus, for example, an integrase recognition region can be formed within the region consisting of the two LTRs joined to one another. Accordingly, a segment of DNA consisting of two LTRs joined to one another can be used as the DNA segment of (D3). It should be noted that the entire region of the two LTRs may not be essential and a DNA segment containing the linking site or the attachment sequence as well as its adjacent region may serve as an integrase recognition region.

For example, the adjacent region of an attachment sequence within an integrase recognition sequence including the attachment sequence may vary depending on the origins of the integrase gene, the LTRs and the like, but in some cases, the adjacent region exists as a region consisting of 20 to 40 bases that includes the attachment sequence (Panganiban, A. T, and Temin, H. M., *Nature*, 306, 155–160, 1983: Duyk. G., et al., *J. Virol.*, 56, 589–599, 1985).

Accordingly, in the vectors in accordance with the present invention, the DNA segment of (D3) may be (a) a DNA segment consisting of two LTRs connected to one another or (b) a DNA segment which partly undergoes deletion, substitution, or addition in a DNA segment consisting of two LTRs connected to one another, and contains an integrase recognition region. The DNA segments described in (b) above which partly undergoes deletion, substitution, or addition in a DNA segment consisting of two LTRs connected to one another includes the situation of a segment containing a portion of LTRs, for example, a segment containing a region consisting of a linking site and its adjacent region or a segment containing a region consisting of an attachment sequence and its adjacent region.

DNA sequences of LTR are described in, for example, *Cell*, 32, 853–869, 1983, and Accession No. AF110968, Y07725 or X94150 of Genebank. These LTRs may be used in the vectors of the present invention. LTRs can also be obtained by, for example, constructing primers based on these known DNA sequences and performing PCR techniques. The resulting LTRs may also be used in the vectors of the present invention.

In most cases, LTRs contain a promoter which enables the expression of the integrase gene. Thus, a plasmid containing a region that consists of two LTRs linked to one another can be used as the vector containing the DNA segment of (D2) which provides the expression control region of the integrase gene. The integrase gene can be expressed even when the promoter in the LTR cannot function due to the type of the host cell or when the vector is intentionally constructed without a promoter, by providing a separate expression control region, such as a promoter, at a location upstream of the integrase gene.

The plasmid vectors of the present invention have an integrase gene incorporated therein so that the integrase gene is expressed in host cells and integrase is synthesized in the cytoplasm. Though it is depending on the origins of the integrase gene, if the integrase has a nuclear localization signal of its own, then it is presumed that the integrase is transported into a nucleus where it recognizes the (D3) region on the plasmid and mediates the integration of the plasmid into the genome of the host cell. However, if the integrase is lacking a nuclear localization signal, or if the integrase is not properly transported into a nucleus despite the presence of a nuclear localization signal, it is desirable to separately add to the plasmid a segment of DNA encoding a nuclear localization signal of integrase. The DNA encoding a nuclear localization signal may include that described, for example, in an article by Nath, S. T. and Nayak, D. P. (Mol. Cell. Biol., 10, 4139–4145, 1990: a list of 14 different sequences is provided) or a nuclear localization signal of SV40 large T antigen described by Kalderon, D. (Cell, 39, 499–509, 1984). These nuclear localization signals may be added to the plasmid at a location upstream and/or downstream of the integrase gene depending on the type of the signal.

Preferably, integrase gene and LTR are derived from retroviruses. Among different retroviruses, they are preferably derived from those belonging to Oncovirinae, more preferably from those belonging to the avian luekosis-sarcoma virus group, and most preferably from Rous sarcoma virus.

The component (D4) will now be described. The component (D4) can be any DNA segment to be desirably integrated into the genome of a certain type of host cells using the vectors of the present invention. While the DNA segment as component (D4) can be arbitrary DNA, it typically has some function and is integrated into the genome in order to express such function. Examples of the functional DNA which can be integrated into the host genome includes a foreign gene encoding a specific protein, DNA involved in the expression of the gene or portions thereof, and DNA encoding antisenses or ribozymes. Examples of the DNA involved in the expression of a foreign gene include promoters, enhancers, terminators, ribosome binding regions, and LCRs (locus control regions). A segment of DNA serving as a marker gene may be added to the DNA segment of (D4) in order to help one determine if the DNA segment of (D4) has been incorporated into a plasmid or if it has been integrated into the genome of host cells.

The DNA components of (D1), (D2), (D3), and (D4) can be inserted into a plasmid by means of ordinary methods which utilize restriction enzymes, ligases, or the like. The restriction enzymes may be selected depending on the type of the basic vector before inserting the DNA components such as (D1) thereinto. Also, in order to enable the easy production of the vector of the present invention in large amounts using bacteria, plasmids with a replication origin essential for the replication of the plasmids in bacterial cells may be used as the vector. In addition, the vectors of the present invention may contain DNA components commonly incorporated into plasmids when they are intended to function as a vector.

For the confirmation if the vectors have been constructed as the vector of the present invention as intended, the constructed vectors may be cut at several sites with restriction enzymes and then electrophoresed. Common techniques including PCR, southern hybridyzation, and base sequencing may also be used in combination for this purpose.

The vectors of the present invention can be introduced into host cells using the same techniques as those used to introduce the common plasmid vectors. Among such techniques are electroporation, calcium phosphate-DNA transfection, liposome, and immunogene technique and the like.

Examples of host cells into which the plasmid vectors of the present invention are to be introduced include, but are not limited to, microorganisms such as E. coli and yeast, cultured plant or animal cells, and cells in living plants or animals. Once introduced into host cells, the vectors of the present invention are efficiently integrated into the genome of host cells with the help of the components such as integrase gene in the vector. Accordingly, transformants transformed by the vectors of the present invention can be obtained.

Particular embodiments of such transformants include TG animals as described below.

Since the vectors of the present invention contain an integrase gene, they are capable of synthesize integrase in host cells, eliminating the necessity to separately introduce integrase into cells. On the contrary, if integrase is to be introduced into the host cells separately, purification of protein, i.e., integrase, is required. This is required every time cells are transfected with the vectors. Purification of a protein generally involves complex procedures, and it is generally easier to make plasmids containing a gene for a particular protein than to purify the protein itself. Thus, the vectors of the present invention are readily constructed, and once constructed, they are readily amplified to large amounts by means of ordinary methods.

It is not necessarily known exactly where the vectors of the present invention are integrated into the genome of host cells. But, the integration does not occur in a completely random manner, namely, the vectors tend to be integrated into specific locations with higher frequency.

(2) TG (Transgenic) Animals and Production Methods thereof.

(i) TG Animals or the Like and Production Methods thereof.

The vectors of the present invention may be used to produce chimeric or TG animals (which may be referred to as "TG animals or the like" hereinafter). The vectors of the present invention can be inserted into a certain type of cells such that a foreign DNA of interest that has previously been incorporated into the vector is integrated into the genome of the animal cells to cause them to transform, resulting in chimeric or TG animals.

Examples of cells into which the vectors of the present invention are to be introduced to produce TG animals or the like include fertilized eggs, non-fertilized eggs, embryonic cells, germline cells and primordial germ cells. The vectors can be introduced into the cells using ordinary methods for introducing plasmid vectors into cells.

The vectors containing the components (D1) through (D4) are used. The DNA segment of (D4), a segment of DNA to be incorporated into TG animals or the like, can be selected depending on the purposes of production of the TG animals or the like. TG animals or the like are used in various studies and industrial applications including identification of cis-acting control elements, analyses of gene functions, production of model animals for human diseases, improvement of breed, production of physiologically active substances, and production of donor animals for organ transplantation. DNA obtained depending on its intended purposes including these applications is incorporated into the vectors having the components (D1), (D2) and (D3) to make a vector having the components (D1), (D2), (D3) and (D4).

Particular embodiments of production methods of TG animals or the like will now be described.

First, a method for producing birds Into which a gene has been introduced as well as a method for making TG animals using such birds will be described as a first embodiment. A plasmid vector containing the components (D1) through (D4) is injected into embryos in eggs of birds to integrate the DNA segment of (D4) into the genome of cells that make up the embryo. The eggs are hatched to obtain individuals into which the DNA segment of (D4) has been incorporated (i.e., a bird into which a foreign DNA has been incorporated).

Examples of birds into which a foreign DNA of interest, is to be incorporated include, but are not limited to, chickens, ostriches, turkeys, ducks, geese, doves, and quails. Among these, chickens, ostriches, turkeys, and ducks are preferred.

A plasmid vector into which DNA to be integrated into birds has been inserted, i.e., a plasmid vector which has the components (D1) through (D4), is prepared and injected into embryos of birds. With respect to the preparation of the plasmid vectors, refer to the description in the above section of "(1) Vectors and Transformants in Accordance with the Present Invention".

The method for producing birds which have incorporated a foreign DNA in accordance with the present invention involves injecting a vector into embryos in eggs. Thus, embryos that can be used in the method for producing the birds include embryos at a development stage within the time range from just before the beginning of incubation period (or immediately after the laying of eggs) to just before hatching. For the purpose of explanation, the time period between a time point immediately before the beginning of incubation and a time point immediately before hatching is divided into the first and second halves, with the first half being earlier than the second, and the embryos in the earlier half are designated as "early embryos" and those in the later half are designated as "late embryos." Although the plasmid vectors may be injected into any embryos in the method of the present invention for producing birds which have incorporated a foreign DNA, the vectors are preferably injected into early embryos.

The vectors can be introduced into the embryos by using methods according to those used to inject conventional plasmid vectors into embryos. For example, the plasmid vectors may be mixed into a biologically acceptable physiological saline or mixed with liposomes to form a solution. Using a glass capillary tube, the vector-containing solution is injected into the early embryos in eggs through a window formed in their shells by removing a part thereof. Alternatively, a vector DNA-tranferrin-poly L lysine complex may be prepared and injected into eggs using a glass capillary tube. The complex enables the efficient introduction of the DNA into cells due to the interaction between transferrin and transferrin receptors that are present on the cell membrane of most cells. While it is preferred to inject the plasmid vectors into early embryos as described above, it is particularly preferred to inject the plasmid vectors into the embryos at as early a developmental stage of the embryos as possible for the purpose of producing TG animals of birds.

Once injected into an embryo, the vectors are introduced into the cells that make up the embryo. The vectors introduced into the cells are then integrated into the genome of the cell, the result being the incorporation of the DNA of interest (i.e., DNA segment of (D4)) into the genome of the cells of the bird embryo. Electroporation may be employed in order to facilitate the introduction of the vectors into cells.

After the vectors are injected into the embryo, the window is sealed with a strip of vinyl tape and incubation is continued until hatching. Accordingly, the individual of birds that have incorporated foreign DNA are obtained. Ordinary methods for detecting DNA that make use of such techniques as PCR and the southern hybridization may be performed on the DNA collected from the cells of the hatched chicks to determine if the DNA of interest has successfully been introduced into the cells of the chick.

Thus, the birds that have incorporated a foreign DNA are obtained by introducing the vectors of the present invention into embryos in the manner described above. They are, in most cases, chimeric animals in which only a part of the cells of the entire body of the individual have incorporated the foreign DNA. The foreign DNA may be incorporated into either somatic cells or germline cells, or it may be incorporated into both types of cells (hereinafter, the individuals which have incorporated foreign DNA into some of their germline cells such as primordial germ cells, spermatocytes, oocytes, sperms, and ova are referred to as germline chimeras, whereas those which have incorporated foreign DNA into some of their somatic cells other than germline cells are referred to as somatic chimeras). In order to increase the likelihood that germline chimeras are obtained when the vectors are injected into embryos, the vectors may be introduced into the embryos on the second day of incubation in the area of germinal crescent where primordial germ cells are concentrated.

Ordinary methods such as PCR may be performed on somatic cells including skin cells and blood cells as well as on sperms and ova to determine which of somatic or germline cells have incorporated the foreign DNA.

The birds so obtained, whose germline cells have incorporated foreign DNA, are allowed to naturally mate or artificially fertilized to produce transgenic animals of birds. Thus, transgenic animals of birds can be made by using an ordinary method in which a germline chimera is selected from those individuals that have incorporated foreign DNA (first generation) in order to obtain TG animals from a germline chimera. Sperms and ova that are produced by germline chimeras include those that have incorporated foreign DNA and those that have not. This means that, for example, when a germline chimera (first generation) and a non-treated individual without introducing the vector of the present invention are crossed, resulting individuals (second generation) include those with incorporated foreign DNA and those without. Of those individuals that have resulted from the crossing between a germline chimera and a non-treated individual, the ones determined to have inherited the foreign DNA are heterozygotic TG animals in which one of homologous chromosomes carries the foreign DNA. By crossing heterozygotic TG animals each resulting from the same pair of a germline chimera and a non-treated individual, and by selecting from the resulting children, homozygotic individuals in which both of homologous chromosomes carry the foreign DNA can be obtained in as short as three generations.

Once TG animals that are heterozygous or homozygous with respect to the incorporated foreign DNA are obtained, these particular lines of TG animals that carry the foreign DNA can be maintained through successive generations using ordinary methods.

Next, a second embodiment of the method for producing birds into which a gene has been incorporated and the method for making TG animals of birds using such birds is described, with the emphasis on the difference from the first embodiment. In the second embodiment, a plasmid vector containing the components (D1) through (D4) is introduced into primordial germ cells that are collected from birds at an early developmental stage so as to integrate the DNA of (D4) into the genome of the primordial germ cells. The primordial germ cells which have incorporated the DNA are injected into early embryos in eggs of other individuals. The eggs containing the embryos are then hatched to provide individuals with an integrated gene.

Generally, primordial germ cells are contained in high concentrations in bird embryos at an early developmental stage. In particular, for example, in the case of chickens, primordial germ cells can be efficiently collected from the blood of embryos 48 to 55 hours after incubation is started. The vectors can be introduced into the primordial germ cells by means of ordinary methods for introducing plasmids. The primordial germ cells into which the vectors have been introduced are injected into embryos in other eggs, and the eggs are then hatched. The primordial germ cells are returned to the early embryos in other eggs since the embryos from which the cells are collected generally do not survive, making it difficult to put the cells back into these embryos.

The individuals hatched from the eggs into which primordial germ cells have been injected include germline chimeras. The germline chimeras that have incorporated foreign DNA can be selected using ordinary methods.

These germline chimeras are allowed to naturally mate or artificially fertilized in the same manner as described in the first embodiment to produce TG animals of birds.

Next, a third embodiment of the method for making TG animals is described. In the third embodiment, a plasmid vector containing the components (D1) through (D4) is injected into testis of males of non-human vertebrates, and the animals injected with the plasmid vector are allowed to naturally mate or artificially fertilized to produce individuals which have incorporated a gene (TG animals).

Vertebrates that can be used in the third embodiment include, but are not limited to, any animals that belong to any of mammals, birds, reptiles, amphibians, and fishes. In particular, mice, cows, goats, sheeps, hogs, and the like are preferred.

In order to introduce the vectors of the present invention into the testes of male vertebrates, for example, vector-containing solutions such as those described in the first embodiment may be prepared and injected into testes using a syringe.

Once injected into a testis, the vectors are introduced into spermatogenic cells, i.e., germline cells in testes, and are then integrated into the genome of the spermatogenic cells. Included among sperms that have divided and differentiated from the spermatogenic cells into the genome of which foreign DNA are integrated are those carrying foreign DNA. This means that heterozygotic transgenic animals are included in the animals of the second generation that result from the mating between a male injected into its testis with vectors and a female. These transgenic animals can be selected according to standard methods that make use of PCR. Ordinary methods may be used for natural mating or artificially fertilizing the animals depending on the type of the vertebrate the animals belong to.

Expression of foreign gene was observed in blastocysts of mice that had developed from eggs fertilized through natural mating using male mice injected with foreign DNA in their testes (Ogawa S., et al., *J. Reprod. Dev.*, 41, 379–382, 1995).

The foreign gene introduced in this manner was not transferred to the progeny in a sufficiently stable manner to ensure making of a line of TG mouse, however.

In contrast, since the vectors of the present invention enables the efficient integration of DNA into the genome of host cells once the DNA is introduced into the host cells, TG mice that stably retains introduced DNA can be produced through natural mating or standard artificial fertilization. Though the embodiment has been described with regard to mice, the technique can widely be applied to any mammals.

(ii) Production of Useful Substances.

The vectors of the present invention can be used to produce useful substances. It has been a common practice to utilize vectors to cause the host cells to transform so that they produce useful substances. In the methods of the present invention, useful substances can also be produced in accordance with the common production methods of useful substances which make use of vectors, except that the vectors of the present invention are used.

A vector is prepared by inserting, as the DNA segment (D4), a segment of DNA encoding a useful protein, as well as an expression control region such as a promoter for allowing the expression of the DNA, into a plasmid vector containing the components (D1), (D2) and (D3). The vector is introduced into host cells to integrate the DNA segment (D4) into the genome of the host cell. The useful protein encoded by the DNA is them expressed. If the DNA segment (D4) is encoding an enzyme, the expression thereof can promote reactions in which the enzyme is involved. This enables the production of useful substances other than proteins.

Examples of host cells into which the vectors of the present invention can be introduced include, but are not limited to, microorganisms such as *E. coli* and yeasts, cultured plant or animal cells, and cells in living plants or animals. When somatic cells of living animals are used as the host cells, somatic chimeras or TG animals can be produced and used to produce useful substances. For example, useful substances may be produced in milk of mammals including cows, goats, sheeps, and hogs, or in eggs of birds including chickens, ostriches, and ducks.

Production of useful substances will now be described more particularly with reference to the embodiments employing birds.

In one embodiment, a characteristic method is exemplified in which a plasmid vector is used which has the components (D1) through (D4) with the DNA segment of (D4) containing a region encoding a protein as well as a region for controlling the expression of the protein. The plasmid vector is injected into a bird embryo to integrate the DNA segment of (D4) into the genome of the cells that make up the embryo. This results in a bird that has incorporated the DNA and thus is capable of producing a useful substance in eggs it produces. Thus, useful substances are obtained.

With regard to the preparation of the plasmid vector containing the components (D1) through (D4), refer to the description in "(1) Vectors and Transformants in Accordance with the Present Invention" as described above. Examples of useful substances that can be produced in eggs of birds include any useful proteins for which DNA can be obtained, or any substances for which DNA can be obtained that encodes for an enzyme enabling the production of the substance. The methods of the present invention are particularly suitable for the production of cytokines, humanized antibodies, hormones, anticoagulation proteins, and vaccines, though the methods are not limited to these substances.

In order to produce useful substances in eggs, an expression control region such as a promoter for a protein abundant in the eggs may be joined upstream of the DNA encoding a protein of interest to serve as the DNA segment of (D4). This plasmid vector is injected into the embryo to facilitate the production of the useful substance. For example, an expression control region containing a promoter for ovalbumin, as well as a segment of DNA that encodes a protein of interest and is situated downstream of the promoter, can be inserted in the plasmid as the DNA segment of (D4). This plasmid vector is introduced into embryos in bird eggs which are in turn hatched to provide individuals that have incorporated foreign DNA. The somatic chimeras selected from the hatched individuals are capable of expressing the useful protein in large amounts in the epithelia of oviducts. As a result to be expected, the useful protein is deposited in the eggs produced by the somatic chimeras. Depending upon the type of the protein to be expressed, it is preferred that the vectors should be introduced into as many cells that are constituting the embryo as possible in order to ensure the stable production of the protein.

Alternatively, germline chimeras may be used to produce TG animals of birds which can produce useful substances in the eggs they lay.

Germline chimeras, heterozygotic transgenic animals, and homozygotic transgenic animals can be obtained in accordance with the methods described in the previous paragraphs of "(i) TG animals or the like and production methods thereof." A segment of DNA containing a region encoding the particular type of protein described above, along with the expression control region associated therewith, can be used as the foreign DNA which is to be incorporated into the animals by using the vectors of the present invention.

In particular, a plasmid vector containing the components (D1) through (D4) is injected into embryos in eggs of birds to integrate the DNA into the genome of cells that are making up the embryo. The DNA segment of (D4) in this case contains a region encoding a protein, as well as a region for controlling the expression of the protein. The eggs are then hatched. From the individuals hatched from the eggs, the birds whose germline cells have incorporated the DNA of (D4) are selected to serve as a first generation. These first generation birds are artificially fertilized or allowed to naturally mate with non-treated individuals to produce birds (i.e., second generation) that are heterozygous with respect to the integrated foreign DNA. The useful substance is subsequently collected from the eggs laid by the heterozygotic transgenic animals of the second generation. Also, a litter of heterozygotic transgenic animals are artificially fertilized or allowed to naturally mate with one another to produce transgenic animals of birds (i.e., third generation) that are either homozygous or heterozygous with respect to the introduced foreign DNA. The useful substance is subsequently collected from the eggs laid by these homozygotic or heterozygotic transgenic animals.

Once TG animals that are heterozygous or homozygous with respect to the integrated foreign DNA are obtained, the particular line of TG animals that carry the foreign DNA of interest can be maintained using ordinary methods, and the homozygotic or heterozygotic TG animals that are of the third or later generations can be used to continuously produce the useful substance.

Alternatively, useful substances may be produced in the following manner: A plasmid vector containing the components (D1) through (D4), wherein the DNA segment of (D4) contains a region encoding a protein as well as a region for controlling the expression of the protein, is introduced into primordial germ cells collected from birds at their early developmental stage and the DNA carried by the plasmid vector is integrated into the genome of the primordial germ cells. The primordial cells which have incorporated the DNA are injected into early embryos in eggs of other individuals. The eggs are hatched subsequently. From the individuals hatched from the eggs, the birds whose germline cells have incorporated the DNA are selected to serve as the first generation. These first generation birds are artificially fertilized or allowed to naturally mate with non-treated individuals to produce birds (i.e., second generation) that are heterozygous with respect to the integrated DNA. The useful substance is subsequently collected from the eggs laid by the heterozygotic transgenic animals of the second generation. Also, a litter of heterozygotic transgenic animals are artificially fertilized or allowed to naturally mate with one another to produce transgenic animals of birds (i.e., third generation) that are either homozygous or heterozygous with respect to the foreign DNA. The useful substance is subsequently collected from the eggs laid by these homozygotic or heterozygotic transgenic animals.

Once TG animals that are heterozygous or homozygous with respect to the incorporated foreign DNA are obtained, the particular lines of TG animals that carry the foreign DNA of interest can be maintained using ordinary methods, and the heterozygotic or homozygotic TG animals that are of the third or later generations can be used to continuously produce the useful substance.

The useful substances produced in the eggs can be collected by means of ordinary methods, depending on the type of the useful substance.

(3) Other Application of the Vectors of the Present Invention.

The vectors of the present invention having the components (D1), (D2), (D3), and (D4) can be used to cause transformation in cells and thus have wide applications in addition to those described above. The DNA of (D4) is selected depending on the type of application.

(i) DNA Vaccines

The vectors of the present invention having the components (D1), (D2), (D3), and (D4) may be used as DNA vaccines. In order to serve as a DNA vaccine, the vector is constructed such that it contains, as the DNA of (D4), a segment of DNA encoding a protein that acts as an antigen in cells of the animals of interest, as well as a DNA segment joined with the segment such as promoter for facilitating the expression of the protein. Many DNA segments encoding such proteins are already known. For example, genes such as those described by Davis, H. L, and McCluskie, M. J. (*Microbes and infection*, 1, 7–21, 1999), which are encoding protective antigens of infectious diseases of human or non-human vertebrates, may be used as the DNA of (D4).

The vectors which are the DNA vaccines are prepared in various forms generally used in application of vaccines including liquid formulations, injections, dry formulations, capsules, gold colloids, powder sand particulates and the like. Preferably, the vectors are prepared in the forms of liquid formulations for oral administration, dry formulations for oral administration, capsules, particulates and injection, and particularly, in the forms of dry formulations for oral administration.

Preferred methods for administering the DNA vaccine include injection and oral administration. In case of injection, the vaccine prepared in the form of injection may be injected into the body of subjects according to ordinary methods. It has been reported that antibodies in blood and secretory IgA were induced by orally administering particulated plasmid DNA (Jones, D. H., et al., *Vaccine*, 15, 814–817, 1997). The vectors of the present invention may be orally administered according to the methods such as those described in this article. Advantages of orally administering DNA vaccines include readiness of administration and reduction in side effects such as inoculation reactions at the site of administration. In addition, oral administration of DNA vaccines is particularly advantageous in that local immunity can be induced, preventing infection of many pathogens that enter from mucosal surface.

The induction of immune responses by the use of plasmids requires large quantities of DNA, thus DNA vaccines have not been put to practical use hitherto. One reason for this is that, once introduced into cells, the plasmid DNA is eliminated in a short period of time. In contrast, the vaccines using the vectors of the present invention make it possible for the plasmids introduced into cells to integrate into the genome of the cell such that the antigens are continuously produced. Accordingly, the vaccines using the vectors of the present invention have the ability to induce strong immune responses by providing strong stimulation to immune systems without requiring large quantities of DNA as in the conventional approaches.

(ii) Gene Therapies for Treating Cancer

The vectors of the present invention can be used for treating cancer by inserting, as the DNA of (D4), a segment of DNA that exhibits activities effective in treating cancer, as will be described in the following, so as to integerate the DNA into the genome of cells. Specific embodiments are described below.

(a) Among methods for treating cancer using the vectors of the present invention are, for example, a method involving expression of antisense RNA for an oncogene, a method in which cancer cells are reverted back to normal cells by introducing an intact tumor suppressor gene thereinto, or a method in which apoptosis is induced to kill cancer cells.

In the method employing antisense RNA, the DNA integrated into the genome of target cells by the vectors of the present invention is transcribed to form antisense RNA for an oncogene. The antisense RNA inhibits the translation of mRNA of the oncogene and thus suppresses the cancer. Examples of genes that can be inserted into the vector as the DNA of (D4) include K-ras for lung cancer, and c-fos or c-myc for breast cancer.

In the method in which cancer cells are reverted to normal cells by introducing an intact tumor suppressor gene into the cancer cells, the tumor suppressor gene is introduced into the cancer cells whose own tumor suppressor gene has undergone deletion or mutation, thereby reducing the tumorigenicity. Examples of genes that can be inserted into the vector as the DNA of (D4) include tumor suppressor genes such as the p53 tumor suppressor gene.

Although much study still needs to be done to fully understand the mechanism by which apoptosis works to eliminate cancer cells, the p53 tumor suppressor gene may be used to induce cell deaths by apoptosis in cancer cells.

(b) The methods for treating cancer using the vectors of the present invention also include treating cancer by introducing a drug metabolizing gene, also referred to as a suicide gene, into cancer cells. In this approach, a gene derived from microorganisms, which normally does not exist in the cells and encodes an enzyme involved in a certain metabolic pathway, is introduced by the vectors of the present invention into cancer cells. A prodrug (of an anti-microbial agent, in general) which is activated/exhibited cytotoxicity by the enzyme is then administered such that the cancer cells that have incorporated the gene are killed selectively. Examples of preferred combinations of a suicide gene and an associated prodrug include thymidine kinase (TK) gene of herpes simplex virus and gancyclovir, TK gene of varicella-zoster virus and 6-methoxypurine arabinonucleoside, cytosine deaminase gene of *E. coli* and 5-fluorocytosine, and purinenucleoside phosphorylase of *E. coli* and 6-methylpurine-2'-deoxyriboside.

(c) The methods for treating cancer using the vectors of the present invention further include enhancing anti-tumor immunity by means of immunogene therapies. Different methods such as those described in the following are employed depending on the type of the target cells to which the gene is introduced.

Effector cells exhibiting cytotoxicity against cancer cells may serve as the target cells into which the vectors of the present invention are to be introduced. Cytokine genes are introduced into the effector cells to enhance their anti-tumor activity. Examples of genes that can be introduced into effector cells include those encoding tumor necrosis factors (TNF), interferon (IFN)-γ, interleukin (IL)-2, IL-7, or IL-12.

Cancer cells themselves may also serve as the target cells into which the vectors of the present invention are to be introduced. Cytokine genes, genes encoding an adhesion molecule, or major histocompatibility complex(MHC)-associated genes and the like are introduced into cultured cancer cells. These cancer cells having genome into which the above genes have been integrated can be used as a vaccine. In particular, examples of cytokine genes include those encoding IL-2, IL-4, IL-6, IL-7, IL-12, TNF, IFN, or granulocyte-macrophage colony-stimulating factor (GM-CSF), genes encoding an adhesion molecule include those encoding CD80, CD86, or ICAM-I, and examples of MHC-associated genes include those belonging to the class I or class II genes.

Alternatively, fibroblasts or antigen-presenting cells may serve as the target cells into which a gene is to be introduced to enhance anti-tumor immunity of cells. Genes encoding tumor-specific antigens or cytokine genes and the like as described above may be introduced into fibroblasts or antigen-presenting cells by means of the vectors of the present invention, and the cells are used as a vaccine.

Alternatively, genes encoding tumor-specific antigens may be inserted into a vector, which in turn is used as a vaccine.

(d) The methods for treating cancer using the vectors of the present invention further include providing resistance to anticancer drugs by means of the vectors of the present invention. Anticancer drug-resistant genes may be introduced into hematopoietic stem cells using the vectors of the present invention to provide the cells with resistance to anticancer drugs such that the bone marrow is protected from the strong effects of chemotherapy against cancer. Anticancer drug-resistant genes include multi-drug resistance (MDR)-1 gene and genes encoding topoisomerases.

(e) One of the countermeasures to cope with the recurrence of leukemia following the bone marrow transplantation is donor lymphocyte transplantation, which counts on the graft-versus-leukemia effects. However, this approach may be accompanied by a side effect of severe graft-versus-host-disease (GVHD). To cope with this, a suicide gene is previously introduced into donor lymphocytes using the vector of the present invention such that, upon occurrence of GVHD, a prodrug would be administered to eradicate the transplanted donor lymphocytes, thus avoiding the side effect.

(iii) Gene Therapies for Treating Infectious Diseases

The vectors of the present invention can be used for treating infectious diseases by inserting as the DNA of (D4) a segment of DNA as will be described below into the vectors of the present invention so as to integrate the DNA into the genome of cells.

The infectious diseases that are particularly difficult to treat include those caused by slow-growing pathogens such as HIV (AIDS) and the hepatitis C virus that are capable of evading the host's immune system. A gene therapy for treating infectious diseases involves introducing into the target cells and expressing DNA encoding a protein or RNA that exhibits the activity to impede the lifecycle of the pathogens. This method is also referred to as "intracellular immunization" since it provides individual cells with resistance to infection by introducing a foreign gene into cells (Baltimore, D., *Nature*, 335, 395–396, 1988).

Examples of DNAs that can be introduced into cells for this purpose include those encoding antisenses, ribozymes, decoys, trans-dominant mutated proteins, single-stranded antibodies specific to a pathogen, and receptors for a pathogen modified to remain in endoplasmic reticulum.

Receptors for pathogen of the secretory form are also considered effective. Further, a method is contemplated in which infected cells are killed at an early time following the infection in order to prevent the growth of the pathogen. Examples of genes used for this purpose include toxic genes such as the A fragment of diphtherotoxins, and suicide genes.

As described in the previous paragraphs of "(i) DNA vaccines" above, vectors into which a gene of a pathogen involved in the protection against infection has been inserted can be used as a vaccine, in addition to the intracellular immunization approach. The use of retroviral vectors that have inserted a foreign gene as a vaccine has been reported by Irwin, M. J. et. al (*J. Virol.*, 68, 5036–5044, 1994). In a similar manner to this, cellular immunity as well as humoral immunity can be induced against a foreign protein expressed in cells using the vectors of the present invention.

(iv) Treatments of Congenital Genetic Disorders

The vectors of the present invention which carry an inherent normal gene as the DNA of (D4) can be used for treating congenital genetic disorders by introducing the vectors into cells of patients suffering a congenital disorder such that the inherent normal gene is expressed in the cells.

One possibility is the treatment of the adenosine deaminase deficiency in which a normal adenosine deaminase gene is introduced to treat the disease.

Safety is one of the most significant concerns in the use of vectors for medical applications. In this regard, unlike retroviral vectors which present the possibility that infectious viruses may arise as a result of homologous recombination, the vectors of the present invention, which essentially are plasmids, are considered safer than the retroviral vectors.

Each of the letters "H", "J", "K", "L", "M", and "P" denotes a base in a segment of the host cell's DNA which serves as a target for the insertion of viral DNA. Each of the letters with an apostrophe denotes a base complementary to the base represented by the same letter, respectively.

Figure 2:
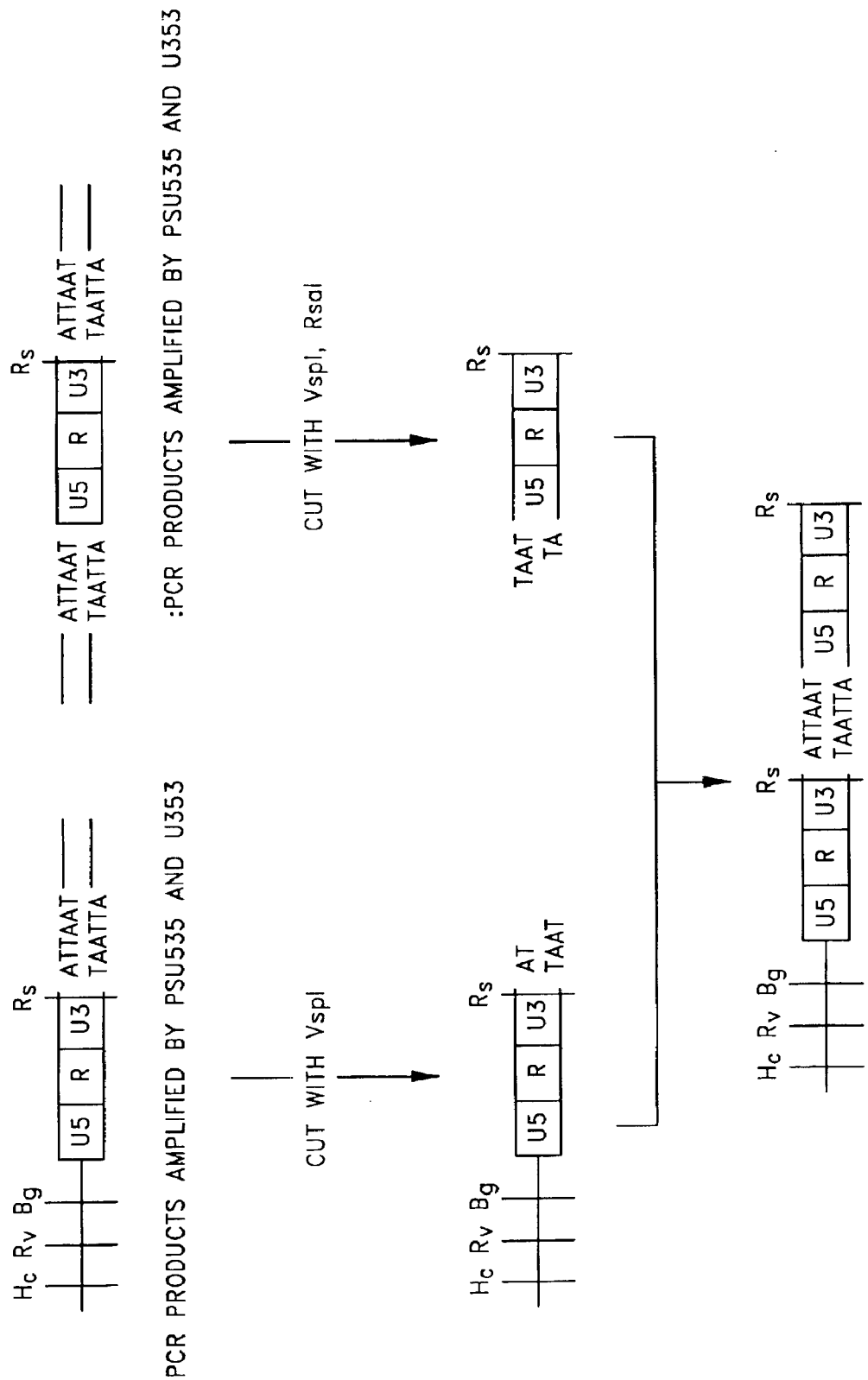

FIG. 2 illustrates how an LTR—LTR linking site, which is found in a double-stranded circular virus when an LTR—LTR is constructed, is formed. Note that sequence originally included in U3 and U5 are partly shown in sequences to be linked in order to show how the LTRs are connected.

Figure 3:
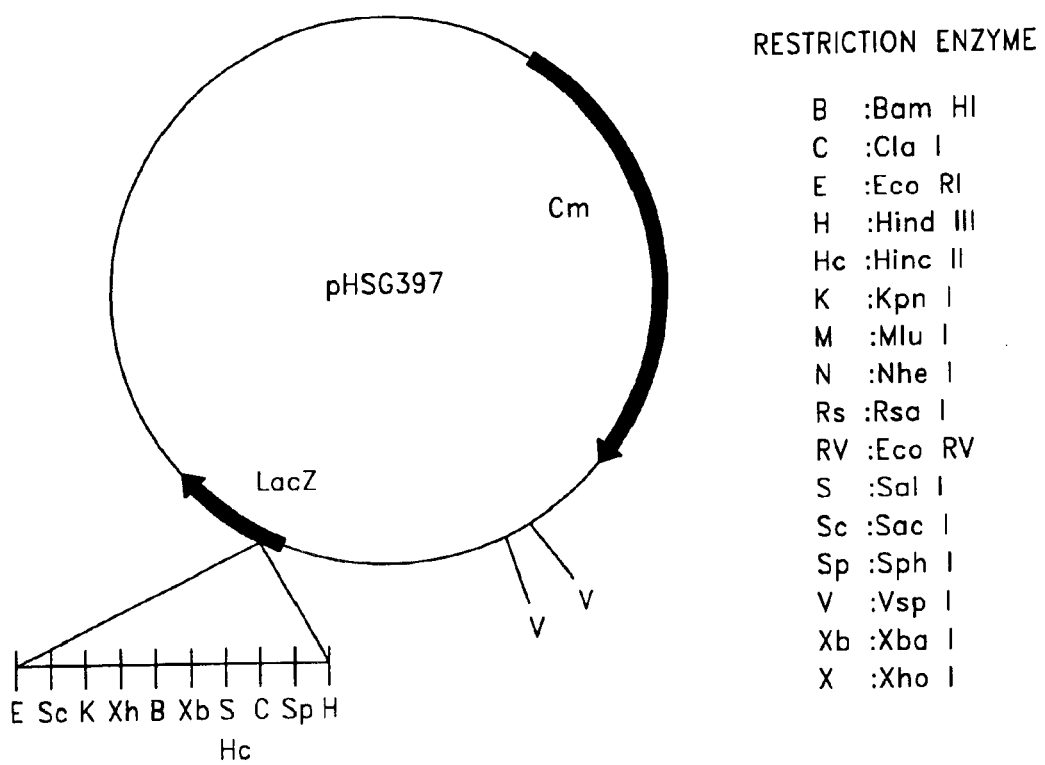

FIG. 3 illustrates structure of plasmid pHSG397.

Figure 4:
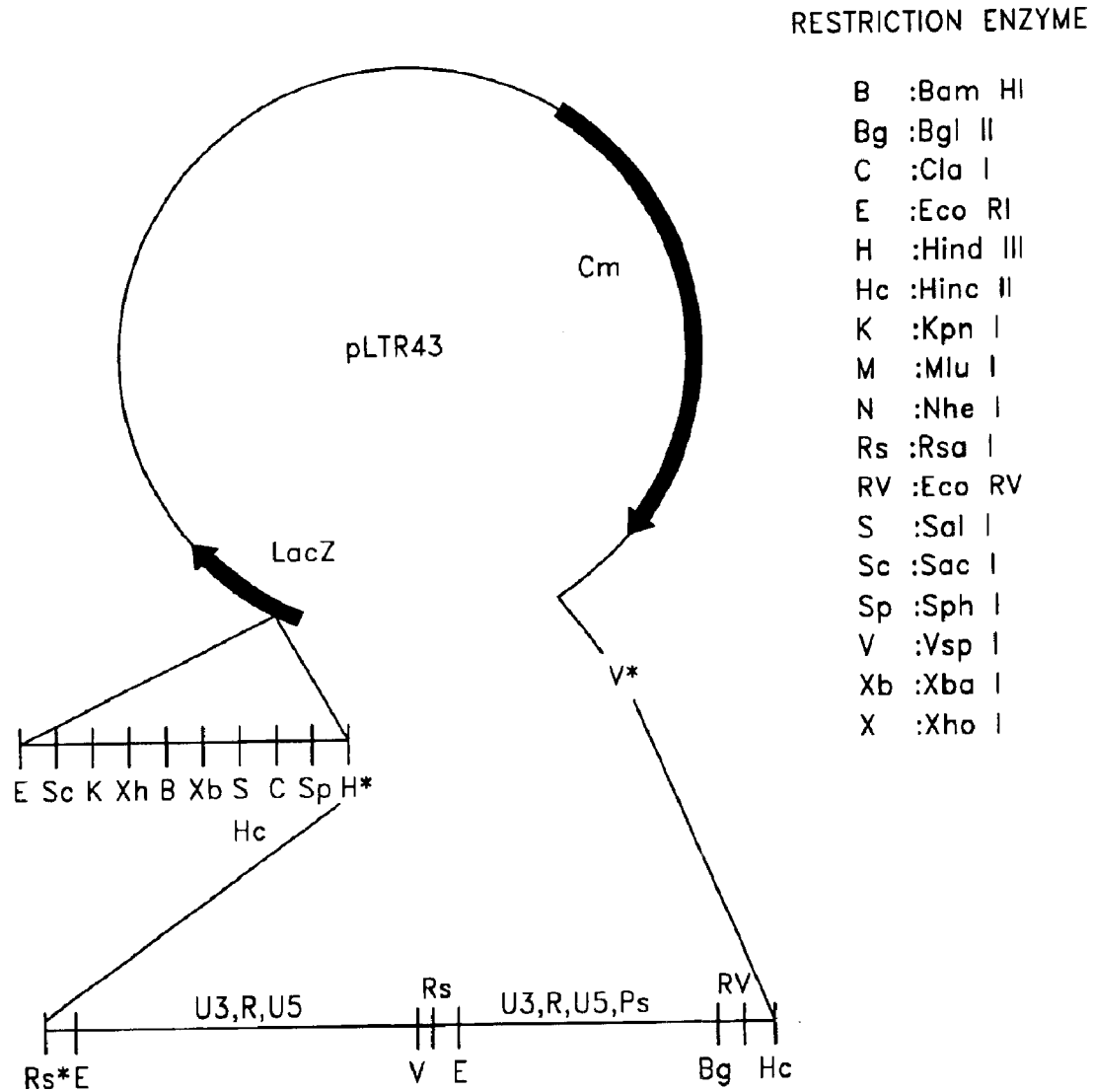

FIG. 4 illustrates structure of plasmid pLTR43.

Figure 5:
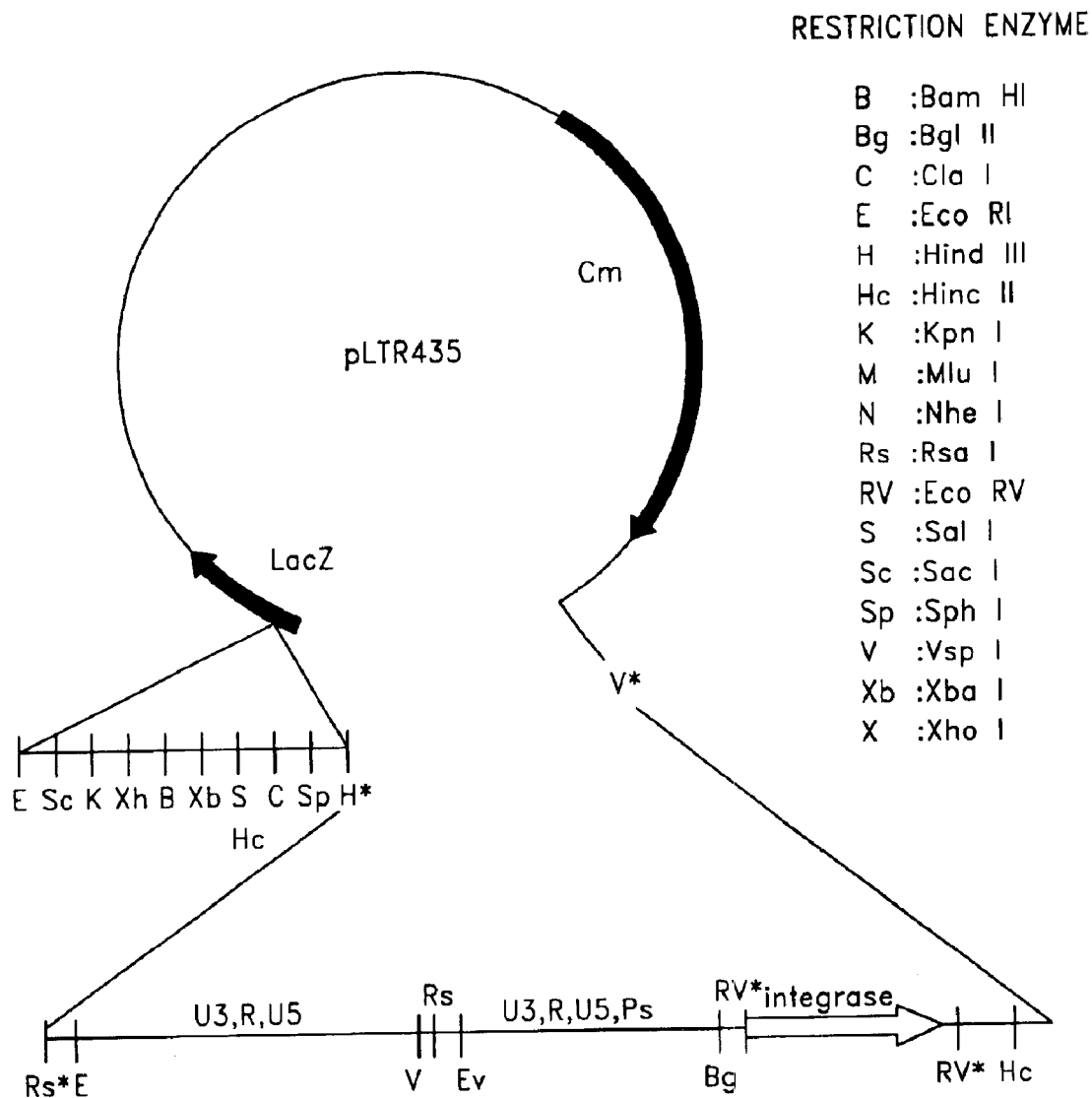

FIG. 5 illustrates structure of plasmid pLTR435.

Figure 6:
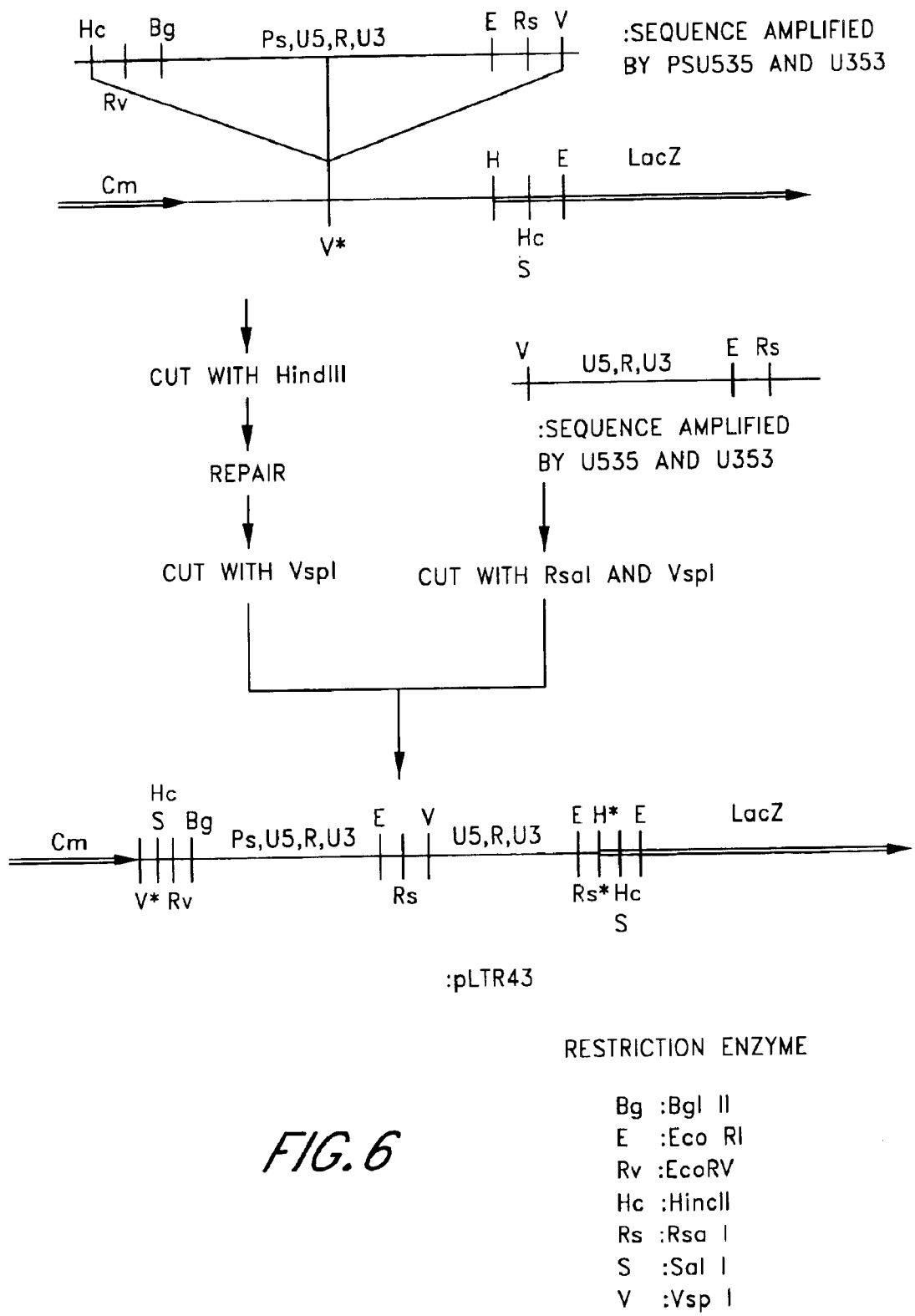

FIG. 6 schematically illustrates a construction scheme of a plasmid vector pLTR43 which has two LTRs in tandem but does not have an integrase gene.

Figure 7:
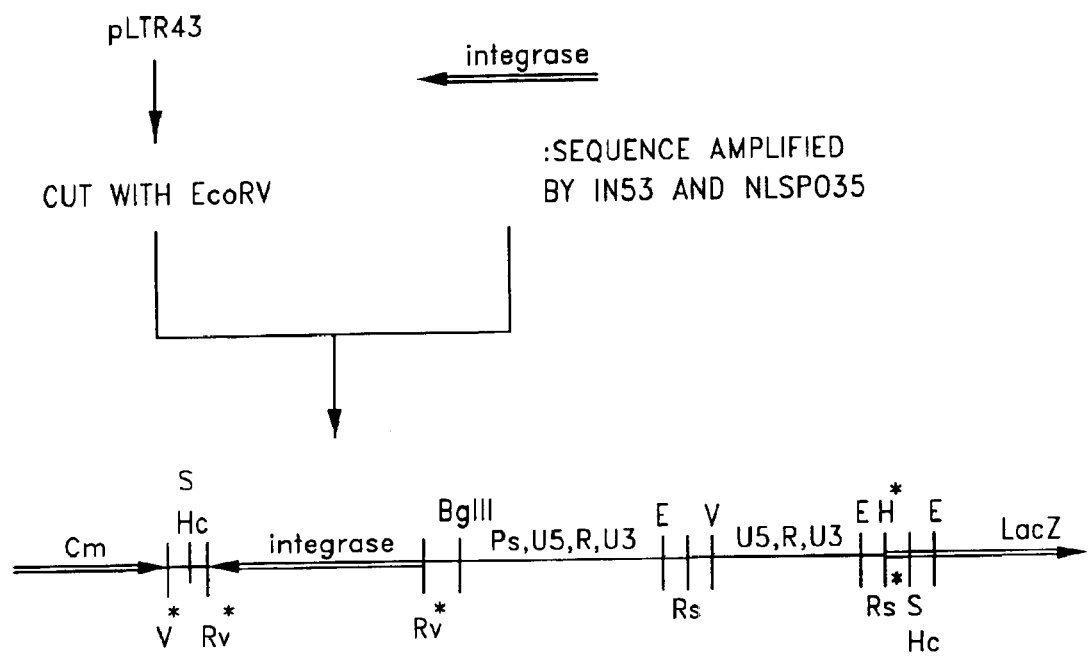

FIG. 7 schematically illustrates a construction scheme of a plasmid vector pLTR435 which has two LTRs in tandem and also has an integrase gene.

Figure 8:
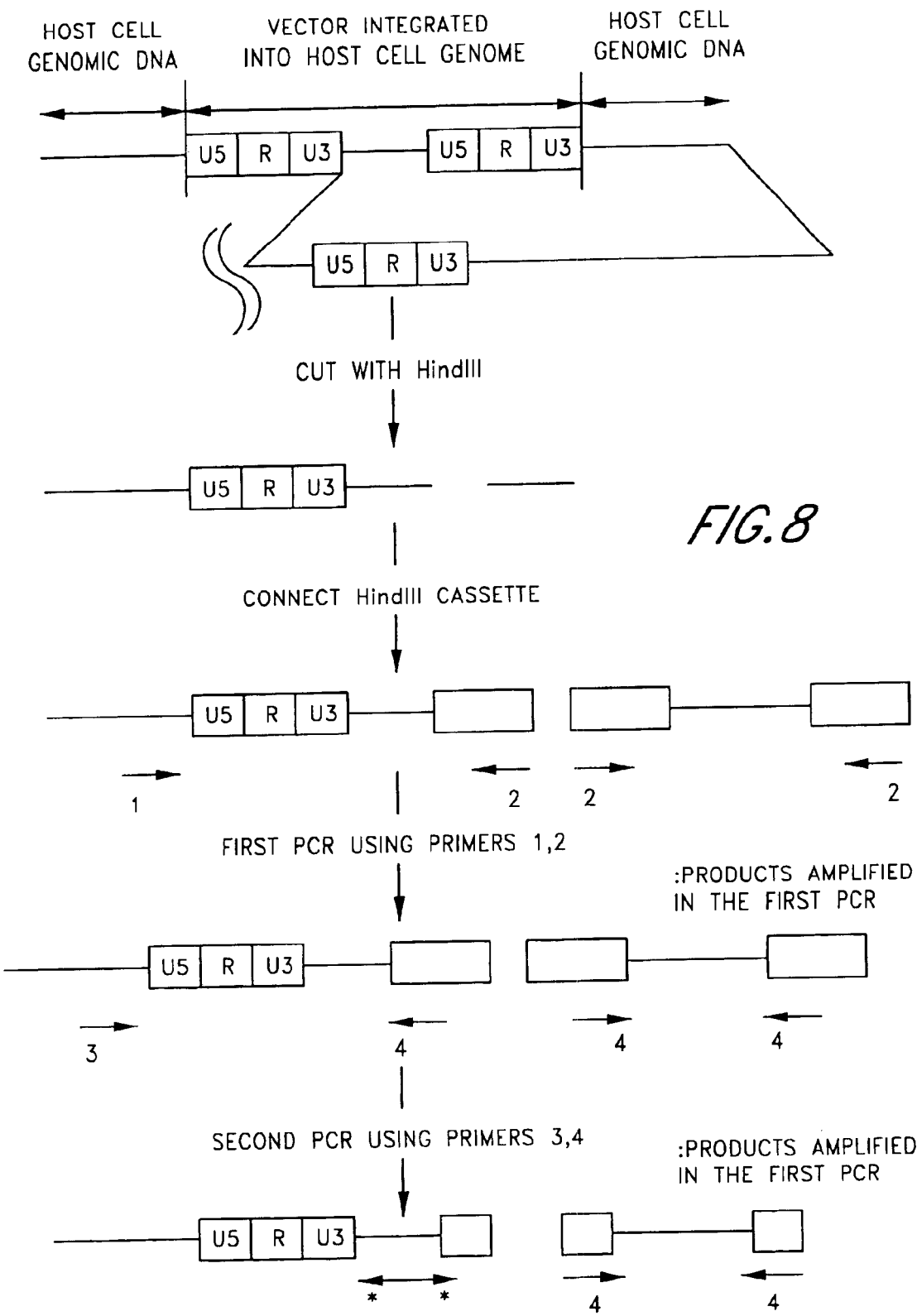

FIG. 8 illustrates a cloning scheme of a region of host cell's DNA including the integration site of the vector, using the TaKaRa LA in vitro cloning kit. In examples 2 and 3, PSU535 was used as primer 1, U535 was used as primer 3, and Cassette Primer C1 and Cassette Primer C2 included in the kit were used as primers 2 and 4, respectively.

Figure 9:
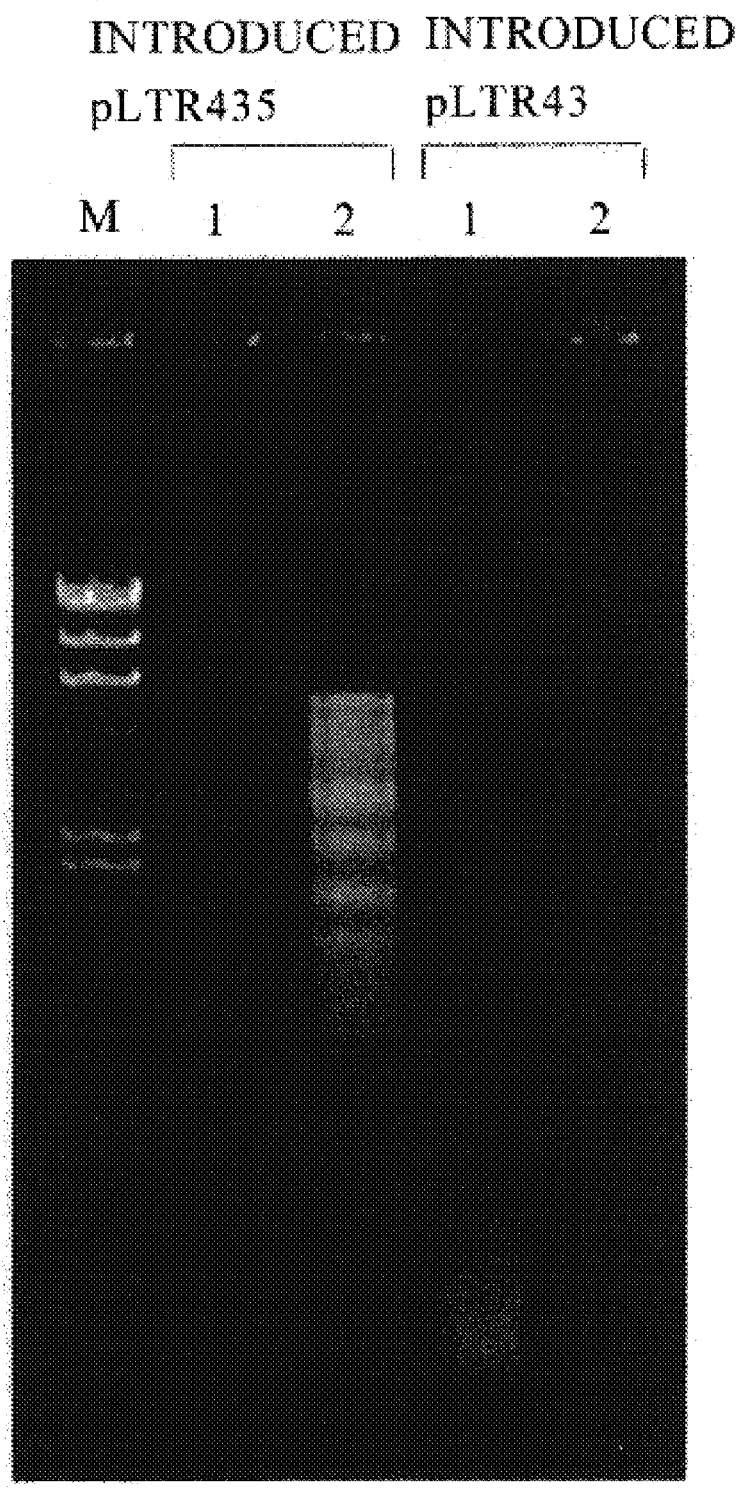

FIG. 9 is a photographic representation showing the result of gel electrophoresis of the products obtained in example 2 after nested PCR.

Lane "M" serves as a marker lane. The numerals "1" and "2" indicate that the lanes are assigned to the products obtained in the first and the second rounds of PCR, respectively. PSU535 and Cassette Primer C1 were used as primer in the first round of PCR. U535 and Cassette Primer C2 were used in the second round of PCR.

Figure 10:
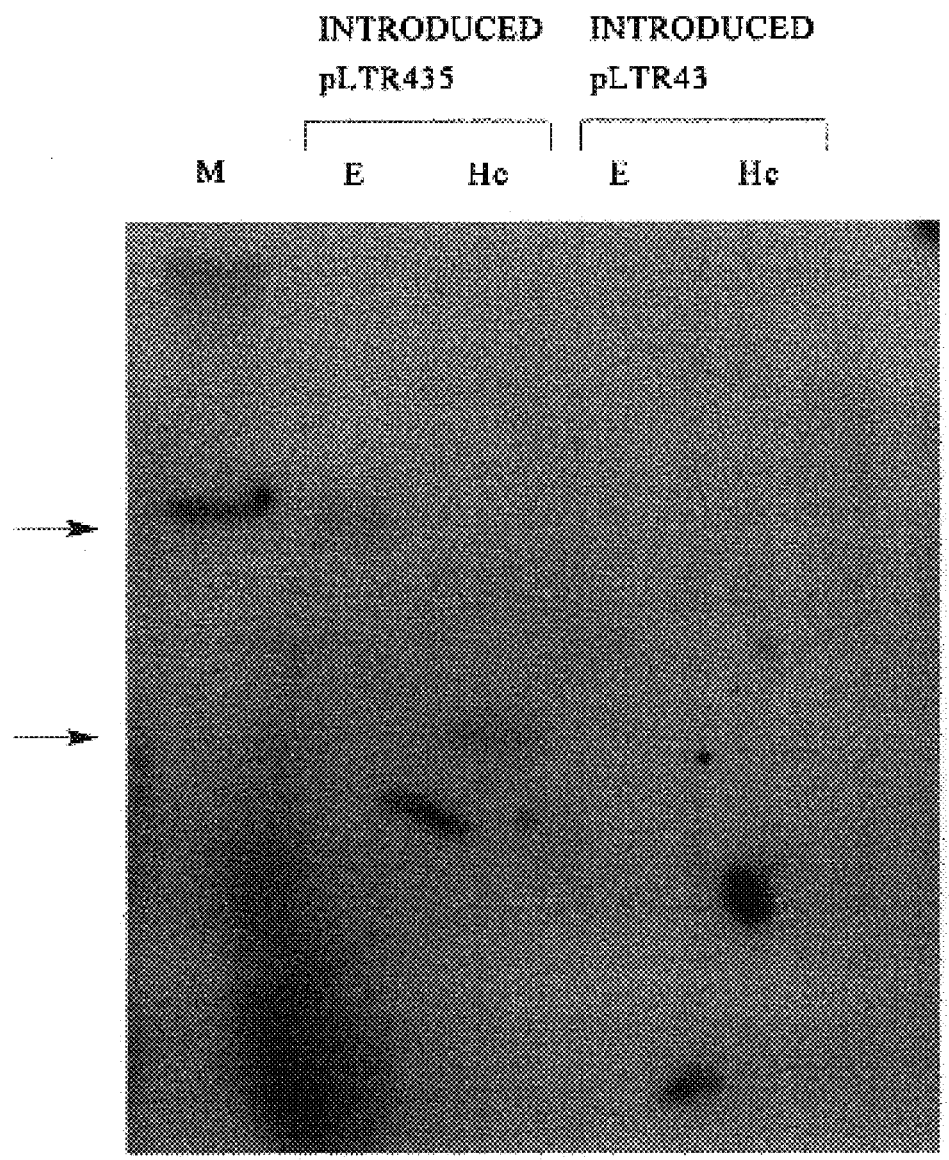

FIG. 10 is a photographic representation of gel electrophoresis showing the result of the southern hybridization in (2-ii-1) in example 2. The arrows indicate the positions of the bands for samples (i.e., analytes) other than the marker.

Marker was loaded in lane M, the product digested with EcoRI was loaded in lane E, and the product digested with HinCII was loaded in lane Hc.

Figure 11:
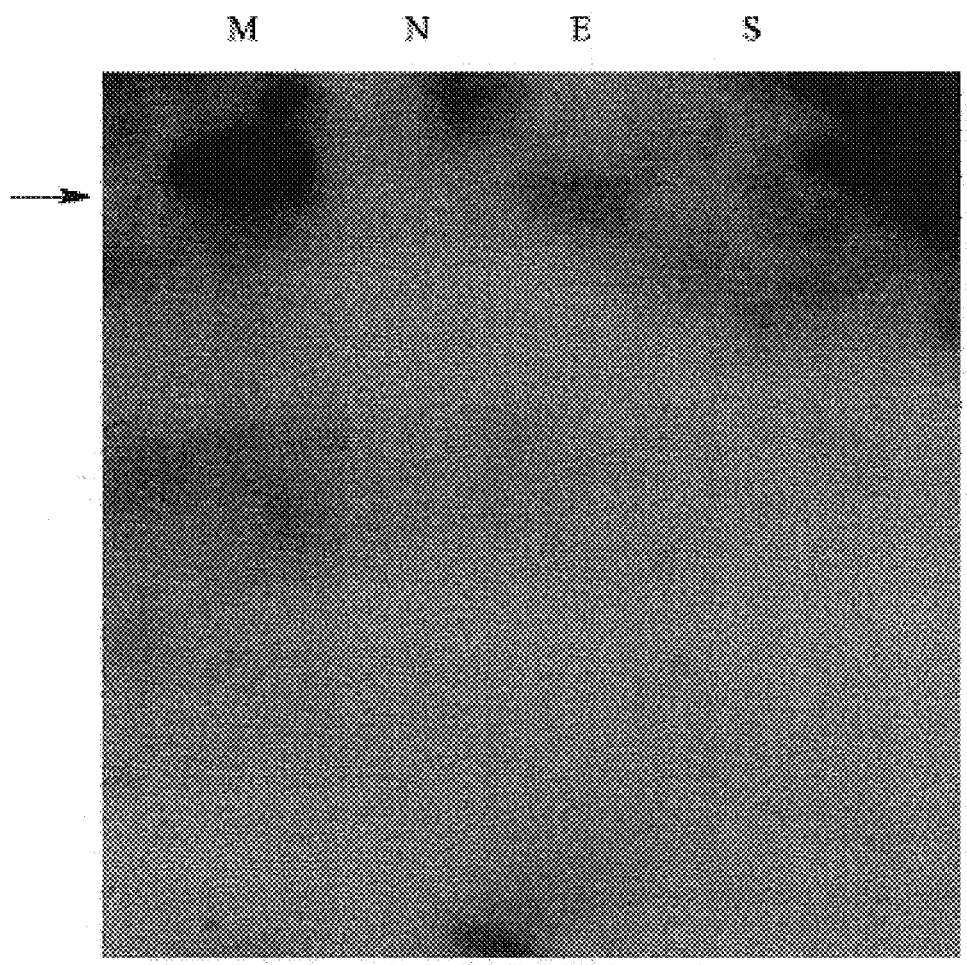

FIG. 11 is a photographic representation of gel electrophoresis showing the result of the southern hybridization in (2-ii-2) in example 2. The arrows indicate the positions of the bands for samples (i.e., analytes) other than the marker.

Marker was loaded in lane M, the product digested with EcoRI was loaded in lane E, the product digested with NheI was loaded in lane N, and the product digested with SalI was loaded in lane S. pLTR435 was cleaved at two locations by EcoRI, at no location by NheI, and at one location by SalI.

Figure 12:
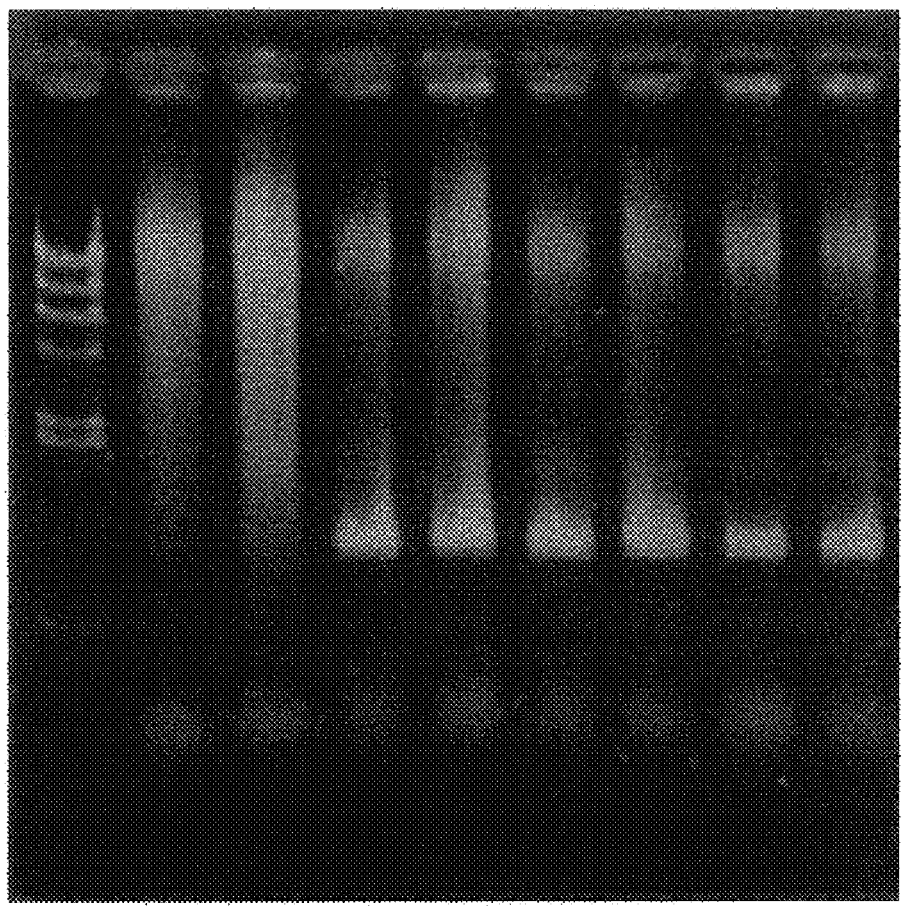

FIG. 12 is a photographic representation showing the result of gel electrophoresis performed on the PCR products of the DNA collected from the blood of chicks in example 3.

Lane M serves as a marker lane. Lane 1 serves as a negative control with no plasmid vector introduced. PCR products of the DNA of the chicks hatched from the eggs into which pLTR43 had been introduced were loaded in lane 2. PCR products of the DNA of the chicks hatched from the eggs into which pLTR435 had been introduced were loaded in lanes 3 to 8.

FIG. 13 shows a comparison in the base sequences of the DNA that was obtained from transgenic chickens and amplified by LA PCR.

The term "HindIII cassette" means a cassette used in the cloning. Framed portion shows HindIII sites formed as a result of ligation between HindIII sites.

Figure 14:
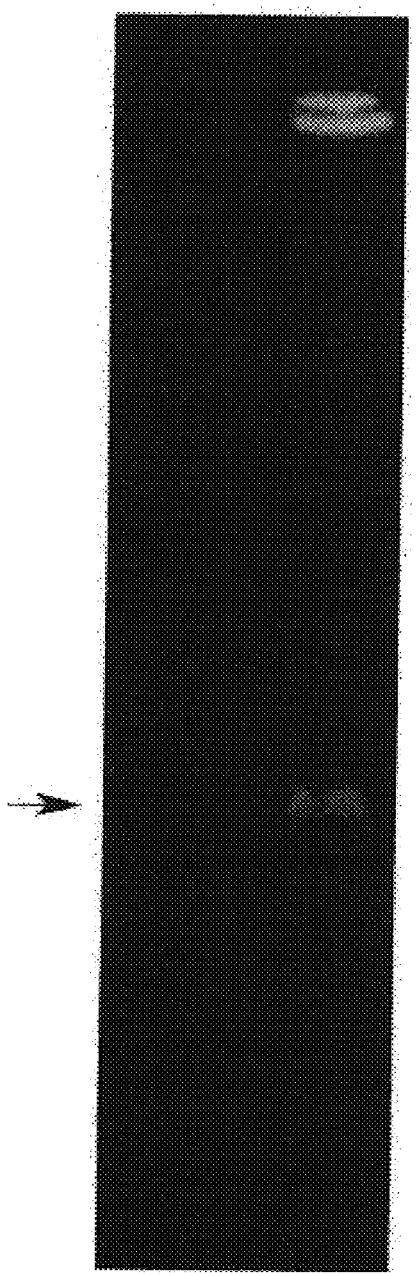

FIG. 14 is a photographic representation showing the result of gel electrophoresis performed on the PCR products of the DNA collected from the sperm of adult chickens in example 3. The arrow indicates the position of the band for samples (i.e., analytes) other than the marker.

Figure 15:
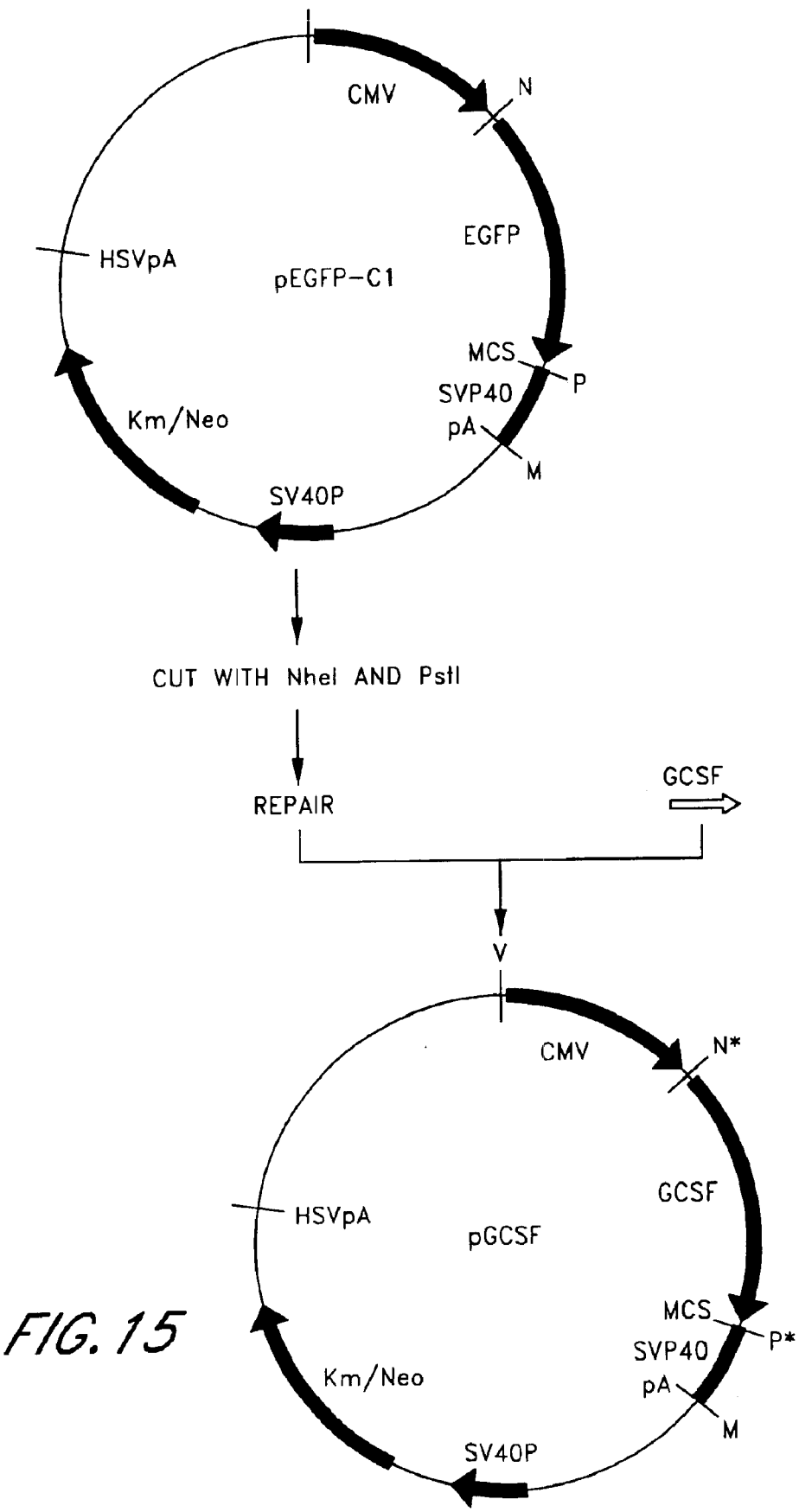

FIG. 15 schematically illustrates steps of constructing plasmid pGCSF from plasmid pEGFP-C1.

FIG. 16 schematically illustrates steps of constructing plasmid pGCSF-ΔIN or plasmid pGCSF-IN from plasmid pGCSF.

Figure 17:
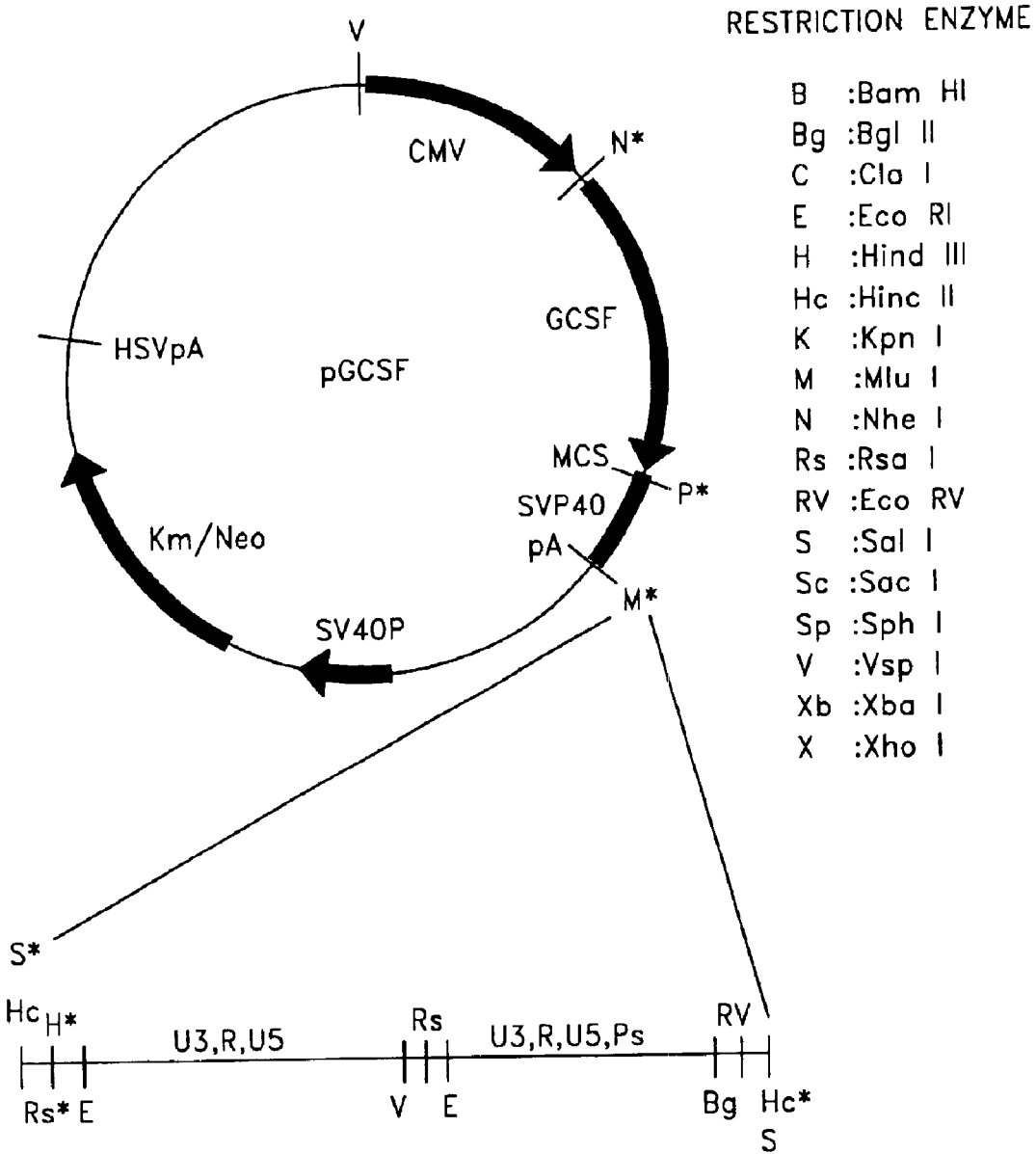

FIG. 17 illustrates the structure of plasmid pGCSF-ΔIN.

Figure 18:
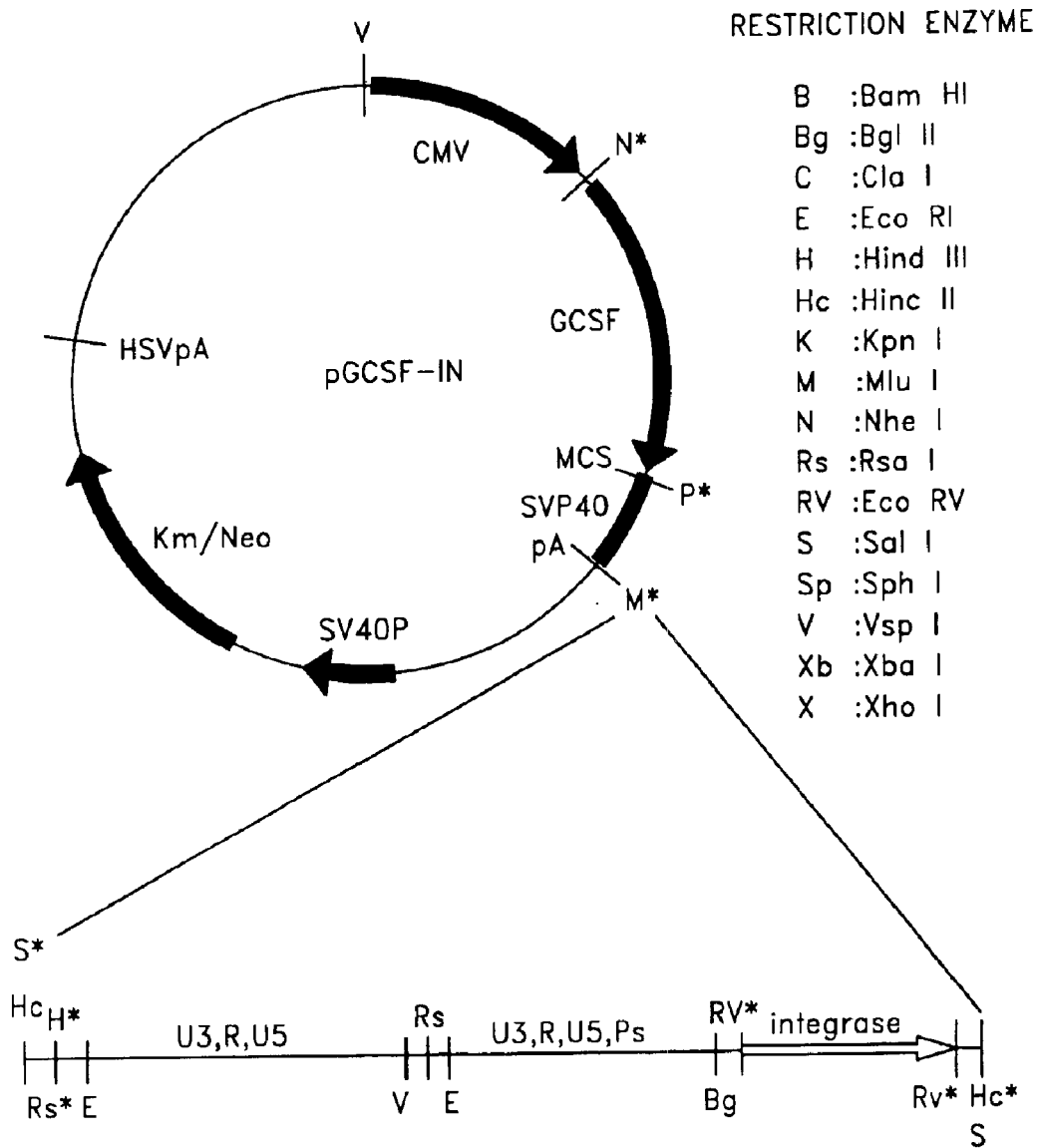

FIG. 18 illustrates the structure of plasmid pGCSF-IN.

Figure 19:
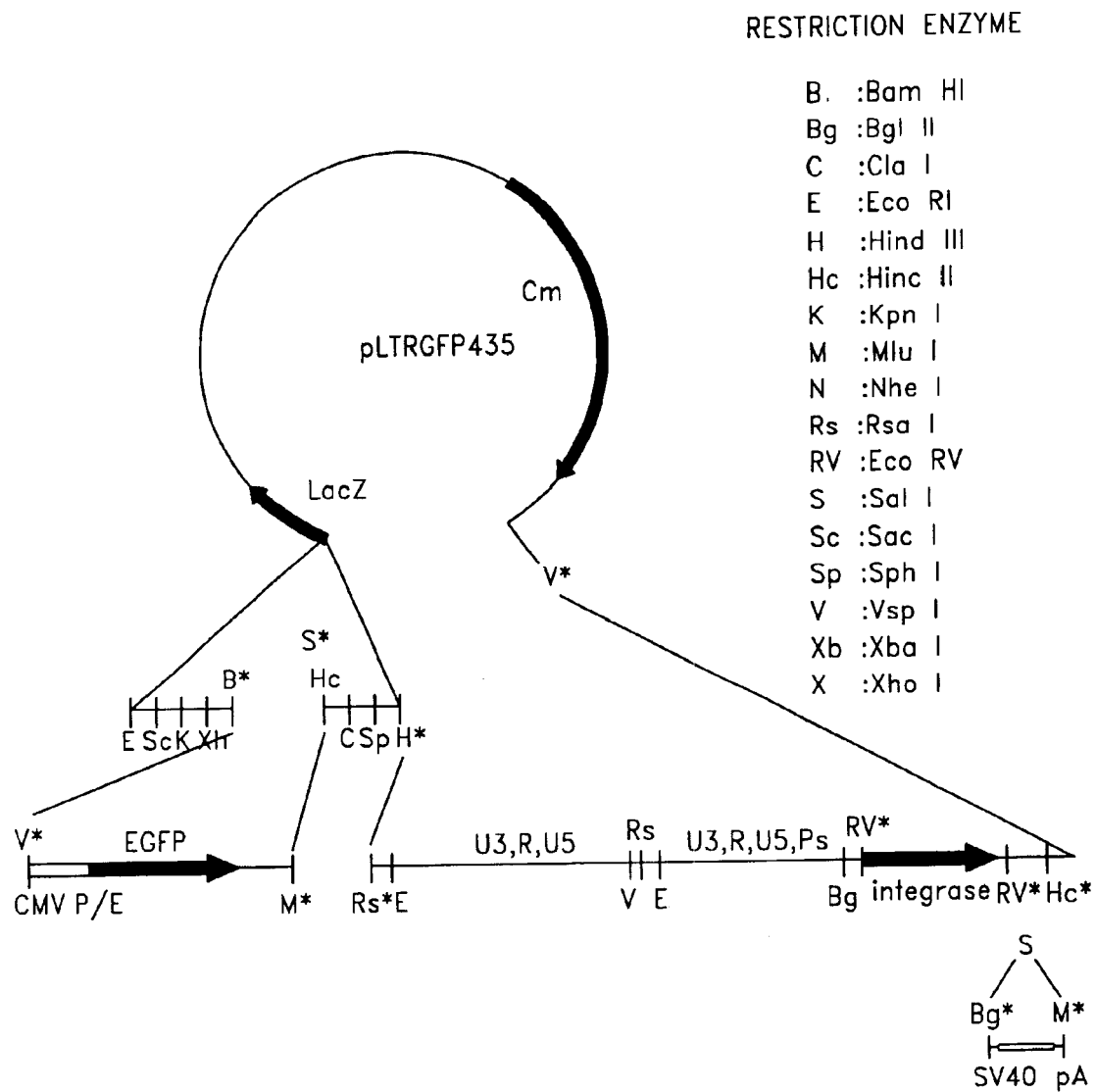

FIG. 19 illustrates the structure of plasmid pLTRGFP435.

FIG. 20 is a micrography of the cells derived from the peripheral blood of a transgenic chicken. Picture "1" is a micrography of the cells derived from the peripheral blood after incubated for two days. Picture "2" is a micrography of the same cells, taken in the same frame as picture "1", with fluorescent light and visible light illuminated thereon. Of the arrows shown in picture "2", larger ones are pointing to typical GFP positive cells and smaller ones to typical GFP negative cells.

Figure 21:
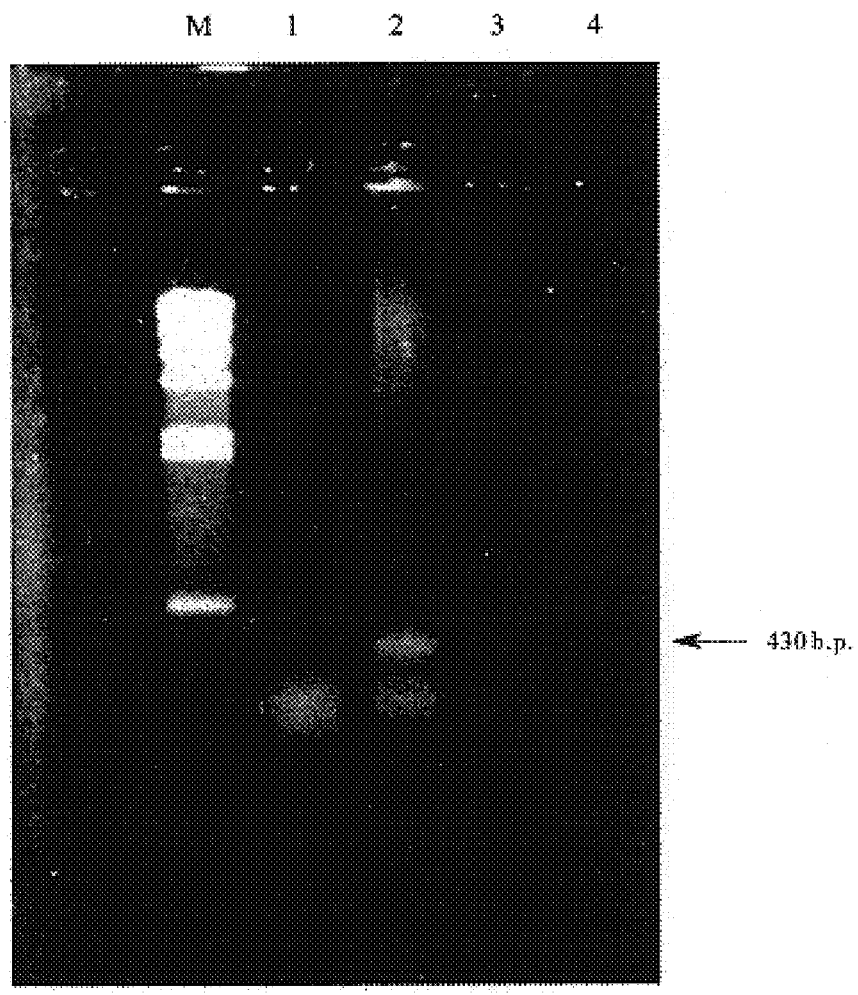

FIG. 21 is a photographic representation showing the result of gel electrophoresis performed on the products obtained in example 5 after PCR. In FIG. 21, lane "M" serves as a marker lane, lanes 1 and 3 show the results of RT-PCR using RNA obtained from lymphocytes before incubation, and lanes 2 and 4 show the results of RT-PCR using RNA obtained from lymphocytes incubated for two days. In lane 3, the result is shown in which the same RNA as that used in lane 1 was treated with RNase without being reverse-transcribed and loaded. In lane 4, the result is shown in which the same RNA as that used in lane 2 was treated with RNase without being reverse-transcribed and loaded.

Figure 22:
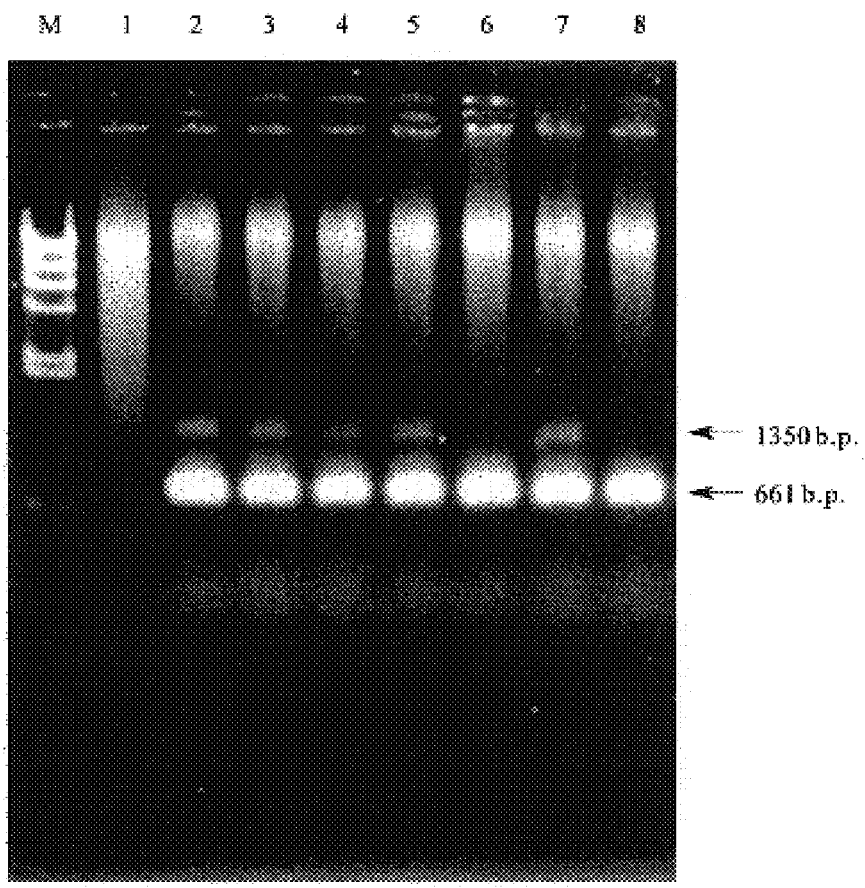

FIG. 22 is a photographic representation showing the result of gel electrophoresis performed on the products obtained in example 6 after PCR. In FIG. 22, lane M serves as a marker lane, and each of lanes 1 to 8 shows an electrophoresis of the PCR product of the genome obtained from each individual.

FIG. 23 shows the structures of pLTRGFP435, which is a plasmid having Ps, and pΔPsGFP435, which is a plasmid that has lost Ps, respectively.

Figure 24:
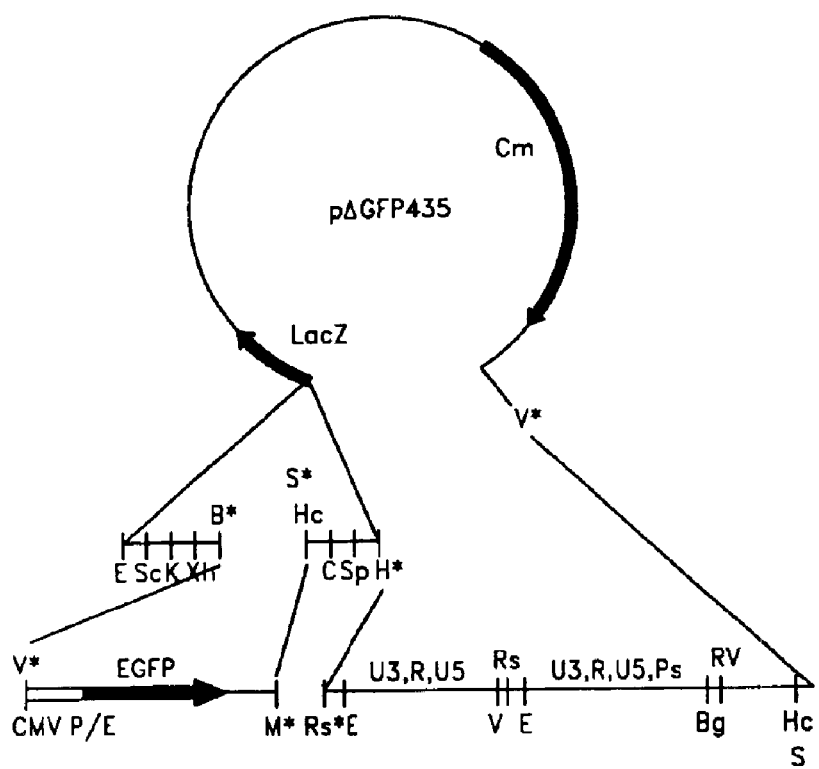

FIG. 24 shows the structure of pΔGFP435, which is a plasmid without an integrase gene.

Figure 25:
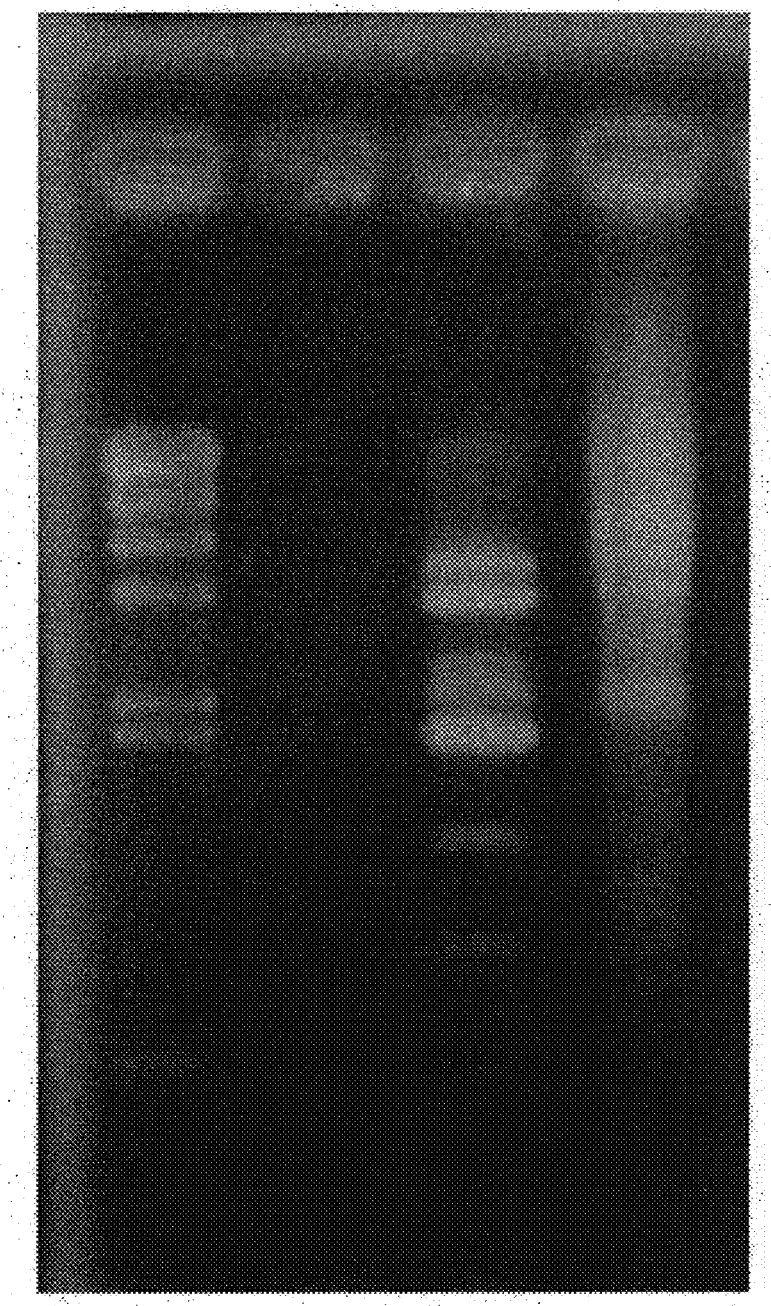

FIG. 25 is a photographic representation showing the result of gel electrophoresis performed on the products obtained in example 7 after PCR. Lane 1 is the PCR product amplified by using, as a template, the genome of a chicken into which pΔGFP435 has been introduced. Lane 2 is the PCR product amplified by using, as a template, the genome of a chicken into which pLTRGFP435 has been introduced. Lane 3 is the PCR product amplified by using, as a template, the genome of a chicken into which pΔPsGFP435 has been introduced.

In the drawings, the restriction enzymes may be indicated by shortened names as listed below. The letters designated by * are the sites that are blunt-ended or connected to a PCR product after cleaved by a corresponding restriction enzyme and are thus no longer cleaved by the enzyme.

B . . . BamHI
C . . . ClaI
E . . . EcoRI
H . . . HindIII
Hc . . . HincII
K . . . KpnI
M . . . MluI
N . . . NheI
Rs . . . RsaI
Rv . . . EcoRV
S . . . SalI
Sc . . . SacI Sp . . . SphI
V . . . VspI
Xb . . . XbaI
Xh . . . XhoI
P . . . PstI
Bg . . . BglII

BEST MODES FOR CARRYING OUT THE INVENTION

The present invention will now be specifically described by examples, which do not limit the present invention.

EXAMPLE 1

Construction of Genome-integration Type Vectors
(1-1) Amplification of LTR Region and Integrase Gene Region Fertilized eggs of white leghorn chicken of Line-M(C/O), which were free from retroviruses, were incubated. On day 12, fibroblasts were prepared from the embryos and were infected with the Rous sarcoma virus (which is referred to as "RSV", hereinafter. The viruses are provided by the Nippon Institute for Biological Science).

Two days after infection, DNA was prepared from the cells according to the standard methods (*Molecular Cloning*, 2nd ed.: Cold Spring Harbor Laboratory Press, 1989., referred to as "M. C." hereinafter).

The primers used in PCR were synthesized according to the RSV nucleotide sequences described in the article by Schwartz, D. E. et. al. (*Cell*, 32, 853–869, 1983). The nucleotide sequences of the synthesized primers are as follows:

U353:
  5'-GGCATTAATGTAGTCTTATGCAATACTCCTG-3' (SEQ ID NO: 1)
PSU535:
  5'-GTTAACGATATCAGATCTGCTTGATCCACCG-GGCGACCAG-3' (SEQ ID NO: 2)
IN53:
  5'-TTGGATCCATGCCCTTGAGAGAGGCTAAAGAT-CTTC-3' (SEQ ID NO: 3) PO35:
  5'-TTTATTTTAACTCTCGTTGGCAGCAAGGGTG -TC -3' (SEQ ID NO: 4)
U535: 5'-GGCATTAATGAAGCCTTCTGCTTCATTCA-3' (SEQ ID NO: 5)
NLSPO35:
  5'-TTTATTTTAAACCTTCCTCTTCTTCTTAGGACT-CTCGTTGGCAGCAAGGGT-3' (SEQ ID NO: 6)

(Description of Primer Sequences)

The order of the nucleotide sequences in the RSV genome shown below assumes that numbering of the bases begins at the first base of the nucleotide sequence of RSV shown in "FIG. 2" in "*Cell*, 32, 853–869, 1983".

4–9th of U353: recognition sequence of restriction enzyme VspI.
7–31st of U353: 9058–9082nd of RSV genome.
1–6th of PSU535: recognition sequence of restriction enzyme HincII.
7–12th of PSU535: recognition sequence of restriction enzyme EcoRV.
13–18th of PSU535: recognition sequence of restriction enzyme BglII.
19th–40th of PSU535: complementary strand of 357–380th of RSV genome.
3–8th of IN53: recognition sequence of restriction enzyme BamHI.
9–11th of IN53: translation initiation codon.
12–36th of IN53: 4119–4243rd of RSV genome.
1–6th of PO35: complementary strand of a polyadenylation signal.
7–33rd of PO35: complementary strand of 5164–5190th of RSV genome.
4–9th of U535: recognition site of restriction enzyme VspI.
7–29th of U535: complementary strand of 79–101st of RSV genome.
1–6th of NLSPO35: complementary strand of a polyadenylation signal.
7–9th of NLSPO35: complementary strand of termination codon.
10–30th of NLSPO35: a sequence encoding the nuclear localization signal of SV40 large T antigen constructed according to the description of *gene* 5th ed., pp292, published by Tokyo Kagaku Dojin, and a codon table for amino acids.
31–51st of PO35: complementary strand of 5164–5187th of RSV genome.

Recognition sequences of restriction enzymes are added to the synthesized primers to facilitate the cloning into plasmids. In addition, a sequence encoding the nuclear localization signal of SV40 large T antigen (Kalderon, D., et al., *Cell*, 39, 499–509, 1984) and a polyadenylation signal were added to the primer NLSPO35, which served as a 3' end primer for cloning the integrase gene. The primers IN53 and PO35, which served as a 5' end primer and a 3' end primer, respectively, for cloning the integrase gene, were designed according to the articles by Schwartz, D. E. et al. (*Cell*, 32, 853–869, 1983) and Hippenmeyer P. J, and Grandgenett, D. P. (*Virology*, 137, 358–370, 1984).

Since the promoter in the LTR are used for transcription of the integrase gene, the primer PSU535 was constructed from a position immediately before the open reading frame of the first protein encoded in the viral genome in the upstream direction. The primers U353 and U535, which served as a 5' end primer and a 3' end primer, respectively, for cloning an LTR region, are designed such that, when a PCR product amplified using the primers U353 and U535 and that amplified using the primers U353 and PSU 535 are joined in tandem, they together form the sequence of the LTR—LTR linking site, which is found in the double stranded, circular DNA form in life cycle of RSV. This is explained in further detail in the following.

Figure 1:
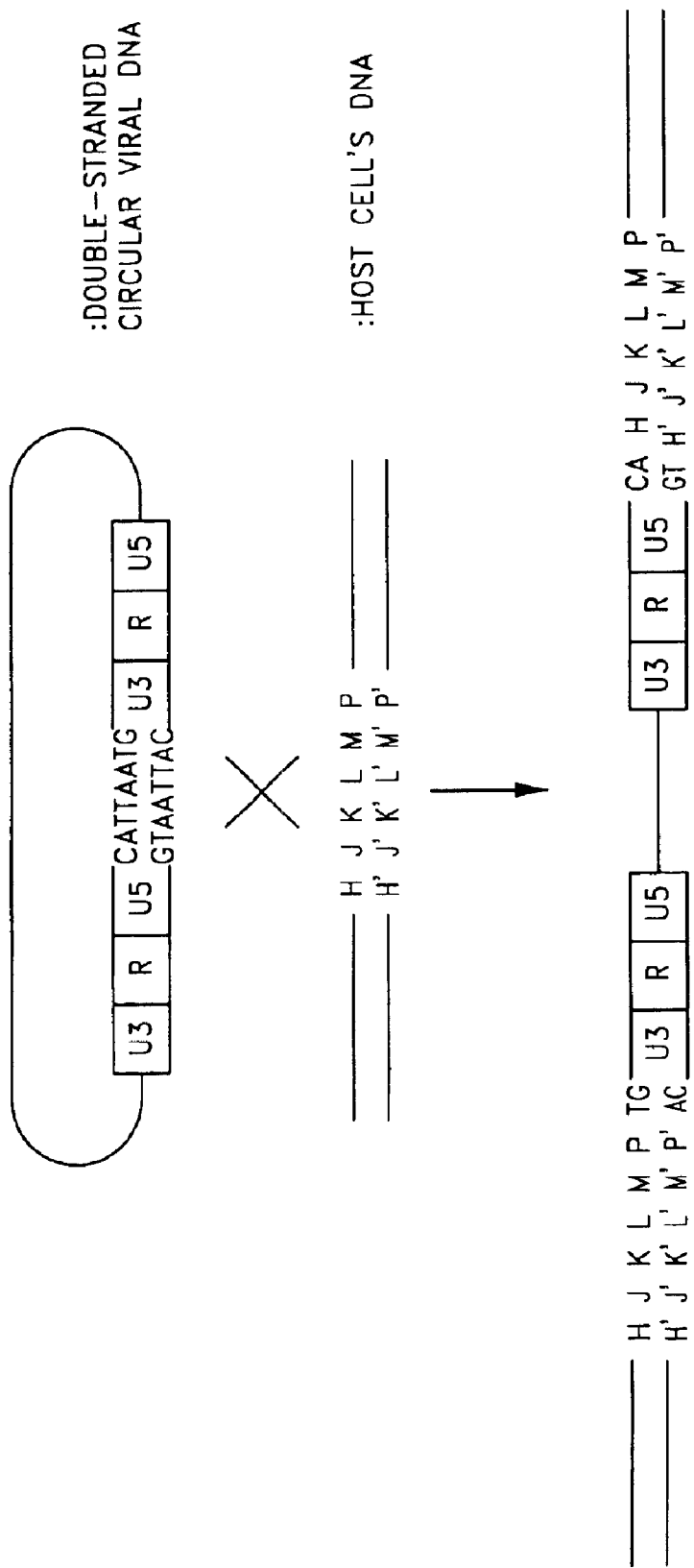
FIG. 1 illustrates the manner in which two bases are lost upon integration of a double-stranded, circular viral DNA into host DNA.

When an RSV forms a double stranded circular DNA in the cell to which it has been infected, it has a sequence "ATTAAT" at the linking site of two LTRs connected in tandem, namely, between U5 and U3 (Schwartz, D. E. et. al., *Proc. Natl. Acad. Sci. USA.*, 74, 994–998. 1977). When a viral DNA is integrated into the host genome to become a provirus, two bases at each end of the viral DNA are deleted. Thus, these sequences are missing in proviruses (*Virology*, 2nd Edition, 1437–1500, edited by Fields, B. N., Knipe, D. M., et al., Raven Press, Ltd., New York, 1990) (See FIG. 1). To form the sequence ATTAAT at the linking site of the LTR—LTR, the recognition sequence ATTAAT for a restriction enzyme VspI was first introduced into the sequence of each of the primers U353 and U535, each of which served as a primer to amplify an LTR region. The amplified PCR products were then cut with the restriction enzyme VspI and the two LTR regions were connected to one another, forming ATTAAT at the linking site of the LTR—LTR (See FIG. 2).

A PCR was performed using the set of these primers and using as a template the DNA obtained from the RSV-infected fibroblasts described above to amplify the LTR regions and the region containing the integrase gene. The nucleotide sequence of the integrase gene is given by SEQ ID NO: 8.

(1-2) Construction of Plasmids

A plasmid pHSG397 (FIG. 3) was cleaved by a restriction enzyme VspI and blunt-ended. A region containing an LTR, which was amplified using PSU535 and U353, was ligated to the blunt-ended plasmid. The plasmid was cleaved by a restriction enzyme HindIII, blunt-ended, and further cleaved by a restriction enzyme VspI. To the resulting product, a segment prepared by cleaving an region containing LTR, which amplified using U535 and U353 with restriction enzymes RsaI and VspI was ligated to form a plasmid pLTR43 that had two LTRs arranged in tandem but did not have an integrase gene (refer to FIG. 4. In FIG. 4, among the letters each corresponding to a type of an enzyme, those designated by * indicate the sites that are blunt-ended or ligated to a PCR product, after cleaved by the corresponding restriction enzyme, and are thus no longer susceptible to the cleaving by the enzyme. The same is true in the other figures). The sequence of the two LTRs joined to one another is given by SEQ ID NO: 7.

The plasmid pLTR43 was cut by a restriction enzyme EcoRV, and a segment containing an integrase gene that had been amplified using IN53 and NLSPO35 was ligated to the ends arising from the cutting by EcoRV to form a final plasmid pLTR435 (refer to FIG. 5).

Protocols for constructing plasmid from pHSG397 to pLTR43, and to pLTR435 are shown in FIG. 6 and in FIG. 7, respectively.

EXAMPLE 2

Transfection and Analysis pLTR43 and pLTR435 were individually introduced into the MEL cells derived from murine Friend leukemia (purchased from RIKEN Cell Bank) using the Transferrin-fection kit (Bender MedSystems).

The cells were passaged such that they were diluted 10-fold from one generation to the next. DNA prepared from the cells of after third passage was subjected to nested PCR and southern hybridization.
(2-i) Nested PCR The DNA containing the vectors prepared from cells was subjected to nested PCR using TaKaRa LA in vitro cloning kit. The principle thereof is shown in FIG. 8. As shown in FIG. 8, PSU535 and U535 was used as a primer 1 and 3 respectively. A Cassette Primer C1 and a Cassette Primer C2 included in the kit were used as primers 2 and 4, respectively.

The size of a fragment or fragments that are amplified by PCR and appear as a band or bands varies depending on the distance between the integrated vector and a recognition sequence for HindIII (shown as a bold arrow designated by ** in FIG. 8). This means that several bands will be detected if the vector is integrated at several specific locations and a smear pattern will appear if the vector is integrated at non-specific locations.

The results of the nested PCR are shown in FIG. 9. For pLTR43, no amplified product was detected in either round of PCR. This implies that pLTR43 was hardly integrated into the genome of the MEL cells. In contrast, an amplified product in the second PCR was detected in the cells into which pLTR435 had been introduced, and was appeared as a smeared band pattern in a gel electrophoresis. The DNA that serves as a template in the PCR has previously been treated with HindIII, a restriction enzyme that does not cut either of pLTR43 or pLTR435 plasmid, thus the detected products are not originating from the introduced plasmid DNA that exists in a circularized form without being integrated into the genome, but rather, they are amplified from the introduced plasmid DNA that has been integrated into the genome. Also, according to the principle depicted in FIG. 8, the smeared band pattern containing strong bands partially seems to indicate that, though the pLTR435 plasmids are integrated into non-specific sites in the genome of the MEL cells, they tend to integrate into particular sites.
(2-ii) Southern Hybridization
(2-ii-1) Twenty μg of DNA prepared from each group of the above-described cells after the third passage was cleaved with restriction enzymes HincII and EcoRI, and then subjected to southern hybridization using standard methods (See "M.C.", supra). The HincII cleaves pLTR43 and pLTR435 at two sites and the EcoRI at three sites.

The results are shown in FIG. 10. As can be seen in FIG. 10, bands were detected only for the DNA prepared from the cells into which pLTR435 had been introduced. This clearly indicates that the pLTR435 plasmids are stably maintained in the cells.

A plasmid pHSG397 cut with an enzyme SalI at one site and labeled with $\alpha$-$^{32}$P-dATP using the TaKaRa random primer DNA labeling kit was used as the probe.
(2-ii-2) Of the DNA samples prepared from each group of the above-described cells after the third passage, the DNA obtained from the cells into which pLTR435 had been introduced was treated with restriction enzymes EcoRI and SalI that cleave pLTR435 at three sites and at one site, respectively, and with a restriction enzyme NheI that does not cleave pLTR435. As in (2-ii-1), the resulting products were subjected to southern hybridization using standard methods (See "M.C.", supra).

The results are shown in FIG. 11. If the plasmids are integrated at random sites of genome, no band will be detected in the hybridization when the plasmids are subjected to be cleaved with the restriction enzyme SalI, which cleaves the plasmid at one specific site, since the distance between the recognition sequences of SalI in the genome and the integrated plasmid varies and the resulting DNA fragments will be dispersed in the gel electrophoresis. Also, if the introduced vectors are not integrated into the genome of the cell and exist in the cells in the form of the plasmids, a band will be detected at a location corresponding to the size of the plasmid. Neither case applies to FIG. 11, however, in which bands were detected, at the locations expected to result from the cleavage of the plasmid by EcoRI, when the DNA sample was cleaved with EcoRI which cleaves the plasmid at multiple sites. This implies that a transfectant is obtained in the genome of which cells pLTR435 has been integrated at non-specific sites.

EXAMPLE 3

Introduction of a Gene into Chickens

Fertilized eggs of white leghorn chicken of Line-M(C/O) described above, which were free from retroviruses, were incubated for 48 hours. On one side of each egg was formed a window having a diameter of about 1 cm, through which a DNA-transferrin-poly L lysine complex prepared by the transferrinfection kit (i.e., the same complex as that used in Example 2 for the purpose of the transfection into MEL cells) was injected into the lower cavity of a blastoderm of embryos at a development stage in an amount of about 2 ul/embryo using a glass capillary tube. The window was sealed with a strip of vinyl tape and incubation was continued until hatching. Blood samples were collected from the wing vein of the chicks two weeks after hatching.

DNA was prepared from the blood using GenomicPrep™ Blood DNA Isolation KIT (Pharmacia), and PCR was performed using primers IN53 and PO35. The results are shown in FIG. 12.

As shown in FIG. 12, no distinct amplified band was observed when the DNA prepared from the chicks hatched from the eggs into which pLTR43 had been injected was used as a template (FIG. 12, lane 2), while amplified bands were observed when the DNA prepared from the chicks hatched from the eggs into which pLTR435 had been injected was used as a template (FIG. 12, lanes 3 to 8: analytes loaded onto each lane were collected from different individuals). This, together with the results of Example 2, confirms that pLTR435 has been integrated into the genome of the cells of the chickens injected with pLTR435 into the lower cavity of blastoderm at embryonic stage.

Further, as in (2-i) in Example, a nested PCR was performed using TaKaRa LA in vitro cloning kit to analyze the nucleotide sequences of the amplified DNA (FIG. 13).

As shown in FIG. 13, the sequence of the HindIII cassette used in the PCR is found in all of the nucleotide sequences of the amplified bands. No homology is, however, seen among the clones in any parts other than the HindIII cassette, however. In addition, the sequences are different from that of the introduced vector. These observations also imply that the introduced pLTR435 has been integrated into the genome of the chickens at non-specific sites.

A male that showed the amplification of bands indicating the presence of pLTR435 was grown until sexually mature, and sperm was collected. DNA was prepared from the sperm and a PCR was performed using IN53 (SEQ ID NO: 3) and PO35 (SEQ ID NO: 4) again (FIG. 14). As shown in FIG. 14, DNA injected into ova has been integrated into the germline cells.

Consequently, the vectors of the present invention enable the integration of foreign DNA in vivo.

EXAMPLE 4

Expression of Feline G-CSF in Cells Derived from Chinese Hamster Ovary (CHO) Cells A plasmid pGCSF was prepared by replacing the EGFP gene on the plasmid pEGFP-C1 (Clontech) with a feline G-CSF gene (FIG. 15). The plasmid was cleaved with a restriction enzyme MluI. A fragment containing an LTR—LTR but not an integrase gene (which is referred to as an LTR—LTR fragment in Example 4) and a fragment containing an LTR—LTR-integrase gene region (which is referred to as an LTR—LTR-integrase fragment in Example 4) were cleaved out from the plasmid pLTR43 and pLTR435, respectively, with a restriction enzyme HincII. Each of the fragments was inserted into the cleaved pGCSF plasmids (FIG. 16) to provide a plasmid pGCSF-ΔIN having the LTR—LTR fragment incorporated therein (FIG. 17) and a plasmid pGCSF-IN having the LTR—LTR-integrase fragment incorporated therein (FIG. 18). Also, as a positive control, a baculovirus vector was used into which a feline G-CSF gene had been inserted according to standard methods using a baculovirus transfer vector pBacPAK1 (Clontech).

Each of these plasmids was transfected to the CHO cells (purchased from RIKEN cell bank) using FuGENE6 (Pharmacia). After the transfection, the activity of G-CSF in the supernatant of each of the cell cultures was determined by measuring the ability of the G-CSF to support the growth of the murine myelocytic cell NFS-60 cells, which are sensitive to the feline G-CSF, using a Cell counting kit-8 (DOJINDO). The Sf21AE cells were infected with the aforementioned recombinant baculovirus and the supernatant of the cell culture was used as a positive control. The results of the measurement are shown in Table 2. Each measurement was undertaken duplicate.

TABLE 2

The results of the G-CSF activities

| | OD value[1] |
|---|---|
| pGCSF - IN first passage | 0.038 |
| | 0.045 |
| pGCSF - IN second passage | 0.072 |
| | 0.073 |
| pGCSF - ΔIN first passage | 0.114 |
| | 0.114 |
| pGCSF - ΔIN second passage | 0.034 |
| | 0.040 |
| Positive control | 0.456 |
| | 0.467 |
| Negative control | -0.015 |
| | -0.014 |

[1]OD values were taken for analytes diluted twofold.

The samples of "first passage" in Table 2 were the supernatants collected from each cell culture two days after transfection. The cells were digested with trypsin and one-fourth of the cells were passaged. After two days, supernatant was collected from each cell culture and was used as the analyte of the "second passage". The supernatant of the culture of untreated CHO cells served as a negative control. As shown in Table 2, with respect to the G-CSF activity in the supernatant of the cultured cells into which pGCSF-ΔIN lacking integrase gene, had been introduced, it has turned out that the G-CSF activity of the second passage was significantly reduced as compared to that of the first passage. In contrast, the G-CSF activity in the supernatant of cultured cells into which pGCSF-IN, which carries the integrase gene, had been introduced was not reduced in the second passage. Rather, the G-CSF activity in the supernatant was increased in the second passage. In the case of the cells transfected with pGCSF-ΔIN, the mean of the measurements for the second passage was about 33%, assuming that the mean of the measurements for the first passage is 100%. In contrast, when the cells were transfected with pGCSF-IN, the mean of the measurements for the second passage was 175%, assuming that the mean of the measurements for the first passage is 100%. This implies that the pGCSF-IN stably exists in the CHO cells and, therefore, stably produces feline G-CSF.

EXAMPLE 5

Expression of Introduced Gene in Chickens

A plasmid pLTRGFP435 was constructed by the insertion of a DNA fragment encoding the green fluorescent protein (GFP) downstream of a promoter/enhancer of cytomegalovirus into a genome-integration type plasmid (FIG. 19). The plasmid was introduced into embryos in the same manner as in the Example 3 to obtain individuals that have incorporated the GFP gene into their genomes.

Lymphocytes were obtained from the peripheral blood of these chickens and were incubated for two days in an RPMI1640 medium containing 20 mg/ml 2-mercaptoethanol, 10 mM lipopolysaccharide, and 10% fetal bovine serum. Expression of GFP in the cells was observed under the a fluorescence microscope. While there was no lymphocyte that emitted green fluorescence before incubation(data not shown), distinctively fluorescent cells were detected after the two-day incubation period as shown in picture "2" in FIG. 20. Picture "1" in FIG. 20 is a micrography of the same cells, taken in the same frame as picture "2".

To further observe the expression of mRNA of GFP, RNA was prepared from the cells used in FIG. 20 and was reverse-transcribed using an oligo-dT primer, followed by performing PCR using primers set within the GFP gene. The primers used are pEGFPF1: CTAGCGCTACCGG-TCGCCACC(SEQ ID NO: 9) and GFP5: GTTGCCGTCCTCCTTGAAGT(SEQ ID NO: 10).

It is expected that this set of the primers amplify a DNA fragment of 430 bp if mRNA of the GFP gene is present.

The results are shown in FIG. 21. In FIG. 21, lane "M" served as a marker lane. Lanes 1 and 3 show the results of RT-PCR (reverse transcription-PCR) using RNA obtained from the lymphocytes before cultivation. Lanes 2 and 4 show the results of RT-PCR using RNA obtained from the lymphocytes cultivated for two days. In lane 3, the same RNA as that used in lane 1 was treated with RNase without being reverse-transcribed and loaded. In lane 4, the same RNA as that used in lane 2 was treated with RNase without being reverse-transcribed and loaded.

In the RT-PCR using RNA obtained from the lymphocytes before cultivation, no band was detected (lane 1), while an expected band was detected in the RT-PCR using RNA obtained from the lymphocytes after cultivation (lane 2). Also, the bands in lane 2 were not amplified after the treatment with RNase (lane 4). This confirms that the bands were not amplified from the templates of genomic DNA contaminating the reaction. These results reflect the observation using fluorescent microscopy described above.

It has been confirmed from the results above that a foreign gene of interest can be integrated into the genome of living organisms and expressed by making use of the plasmids of the present invention.

EXAMPLE 6

Transmission of Introduced Genes to Chickens of the Subsequent Generations (Establishing TG Chickens)

As shown in Example 3 above, the injection of the vectors of the present invention into the lower cavity of a blastoderm in a developing chicken egg appeared to have caused the DNA to be integrated not only into the genome of somatic cells but also into the genome of germline cells of the hatched chicks. Then, an artificial fertilization was carried out between individuals with a GFP gene integrated thereinto and untreated individuals with no GFP gene introduced thereinto. The fertilized eggs that were subsequently laid were artificially hatched to determine if the introduced DNA was transmitted to the individuals of the second generation.

The test was conducted as follows: DNA was extracted from the blood samples collected in the same manner as in Example 3 above. PCR was performed on the DNA which served as a template using primers PO35(SEQ ID NO: 4) and U553: TTGGTGTGCACCTGGGTTGAT(SEQ ID NO: 11) in order to detect the integration of the introduced gene.

At the same time, a set of primers were set at a region upstream of the 5' end of the ovalbumin gene as an internal control to determine if the PCR reaction would proceed properly. Both PCRs were performed in the same test tube. A band will be detected as 1350 bp if the former gene is amplified, while a band will be detected as 661 bp if the latter gene is amplified.

FIG. 22 shows representative data of electrophoresis of each individual. In FIG. 22, lane "M" serves as a marker lane. Each of lanes 1 to 8 shows an electrophoresis of the PCR product of the genome obtained from each individual.

In lane 1, no band is detected for either of the two PCR products, so determined that PCR was imperfect. Thus, such an individual is dealt as being undiscriminating. For individuals of lanes 6 and 8, bands corresponding to the internal control are detected while no band is detected at 1350 bp. This suggests that the introduced gene has not transmitted to these individuals. In contrast, for individuals of lanes 2 to 5 and lane 7, both bands are detected, indicating that the introduced gene has successfully been transmitted. The transmission of the introduced gene to offsprings was observed in thirteen individuals out of the twenty-four individuals in this analysis. Thus, the efficiency with which the introduced gene is transmitted to offsprings is roughly one-half.

Accordingly, it has become apparent from the results above that constructing a TG chicken, which has been considered difficult heretofore, is significantly facilitated by using the vectors of the present invention.

EXAMPLE 7

Integration of a Gene into the Genome of a Chicken Using a Plasmid Lacking a Non-coding Region Including a Packaging Signal In general, it is preferred that a plasmid does not contain unnecessary sequences when it is desired to incorporate a larger foreign gene due to the limitation of the entire size of plasmids. The region extending from a position downstream of the LTRs to a translation initiation site of polymerase including a packaging signal (designated by Ps) is left intact in the genome-integration type plasmids used in Examples 1 through 6 above for avoiding the influences in the transcription caused by the non-coding region. In this example, plasmids lacking this region are tested for their ability to integrate into genome.

A construction of plasmid pΔPsGFP435 lacking Ps is shown in FIG. 23. This plasmid and pLTRGFP435, which has Ps, as well as pΔGFP435, which does not have an integrase gene and serves as a negative control (FIG. 24), were independently injected into the lower cavity of chicken embryo blastoderm using a glass capillary tube as in Example 3 above. The injected plasmids were introduced into cells by electroporation using a gene-introducing apparatus CUY21(Type EDIT, BEX). PCR was performed using the DNA prepared from the blood cells of the two week-old chicks to determine if the plasmids had been integrated into the genome. The PCR was performed in the same manner as in Example 2 above except that the genome was cleaved with a restriction enzyme XbaI and primers PEGF1: ATG-GTGAGCAAGGGCGAGGAGCTGTTCACCGGGGTG (SEQ ID NO: 12) and PEGF2: GTCGAGCTGGACGGC-GACGT (SEQ ID NO: 13) were used as the primers 1 and 3, respectively.

The results are shown in FIG. 25. Lane 1 is a PCR product amplified by using, as a template, the genome of a chicken into which pΔGFP435 has been introduced. Lane 2 is a PCR product amplified by using, as a template, the genome of a chicken into which pLTRGFP435 has been introduced. Lane 3 is a PCR product amplified by using, as a template, the genome of a chicken into which pΔPsGFP435 has been introduced.

As shown in FIG. 25, no band was detected appeared in the PCR for the negative control into which pΔGFP435 had been introduced. In contrast, PCR products were detected as a smeared band in the individual into which pΔPsGFP435 had been introduced, as well as in the individual into which pLTRGFP435 had been introduced, suggesting that integration occurred at random sites of genome. This also suggests that pΔPsGFP435, lacking Ps, may also be effectively integrated into genome.

<Sequence Listing Free Text>

The free text description in item <223> of the sequence listing incorporated in this specification is provided below.
(SEQ ID NO: 1)
Designed PCR primer including 3' region of U3 and VspI restriction enzyme site to multiply RSV LTR.
(SEQ ID NO: 2)
Designed PCR primer including 5' non coding region of p19 gene, HincII, EcoRV and BglII restriction enzyme site to multiply RSV LTR and down stream region of LTR.
(SEQ ID NO: 3)
Designed PCR primer including 5' region of RSV integrase gene and BamHI restriction enzyme site to multiply RSV integrase gene.
(SEQ ID NO: 4)
Designed PCR primer including 3' region of RSV integrase gene, polyA signal to multiply RSV integrase gene.
(SEQ ID NO: 5)
Designed PCR primer including 5' region of U5 and VspI restriction enzyme site to multiply RSV LTR.
(SEQ ID NO: 6)
Designed PCR primer including 3' region of RSV integrase gene, polyA signal, nuclear localization signal of SV40 large T antigen to multiply RSV integrase gene.
(SEQ ID NO: 7)
A part of circular form of RSV DNA, tandem repeat LTRs and adjacent non coding region.
(SEQ ID NO: 9)
Designed PCR primer including 5' region of GFP gene and a part of NheI restriction enzyme site to multiply GFP gene.
(SEQ ID NO: 10)
Designed PCR primer including antisense sequence of GFP ORF to multiply a part of GFP gene.
(SEQ ID NO: 11)
Designed PCR primer including U5 region LTR sequence to multiply a part of integrated plasmid vecter.
(SEQ ID NO: 12)
Designed PCR primer including 5' end of GFP ORF sequence to multiply a part of GFP gene.
(SEQ ID NO: 13)
Designed PCR primer including a part of GFP ORF sequence to multiply a part of GFP gene.

Industrial Applicability

The present invention has the following prime advantages that contribute industrial applicability.
(1) The present invention makes it possible to integrate a DNA of interest into the genome of host cells with great efficiency. Also, any DNA of interest can be integrated into the genome either in vitro or in vivo.
(2) The present invention provides stable transformants by integrating a foreign DNA into the genome. Also, the present invention makes it possible to produce stable TG animals easily.
(3) The vectors of the present invention can be constructed more easily as compared to viral vectors because of their nature as plasmids and because they can be constructed using known plasmids. Also, once constructed, the present vectors are easy to produce in large quantities.
(4) Plasmids are not pathogenic per se. This ensures the safety of the vector.
(5) In contrast to the retroviral vectors, the vectors of the present invention can employ strong promoters.
(6) Large fragments of DNA can be inserted by using the vectors of the present invention. For example, a fragment of foreign DNA as large as 9 kb can be inserted by the present vectors constructed based on pUC plasmids, and a DNA fragment as large as 19 kb can be inserted by the present vectors constructed based on pBR plasmids.
(7) The likelihood that the vector DNA is lost through the growth of cells is smaller as compared to the conventional vectors since the vectors of the present invention, once introduced into cells, are integrated into the genome with higher frequency. Accordingly, stable production of useful substances using transformants is expected.
(8) Unlike the conventional vectors constructed based on viruses, the vectors of the present invention, which are composed of DNA, are less likely to be eliminated by the immune system of living organisms, enabling a repeated administration to living organisms.

The invention may be embodied in other specific forms without departing from the spirit or essential characteristics thereof. Thus, the embodiments described above are construed only as illustrative and not restrictive. The scope of the invention is defined by the appended claims and is not limited to the embodiments described in the specification. Any equivalents provided by making various changes and modifications to the invention are within the scope of the invention.

What is claimed is:

1. A plasmid vector comprising:
   (D1) a retroviral integrase gene;
   (D2) a segment of DNA forming a region for controlling the expression of the integrase gene; and
   (D3) a segment of DNA serving as an integrase recognition region when the integrase resulting from the expression of D1 catalyzes integration, wherein the integrase recognition region (D3) comprises a connecting sequence of terminal bases formed when one long terminal repeat (LTR) is joined to another LTR.

2. The plasmid vector of claim 1 further comprising (D4) a segment of DNA to be integrated into the genome of host cells.

3. The plasmid vector according to claim 1, wherein the integrase recognition region (D3) comprises a region formed by two LTRs joined together, and wherein both of the DNA segments (D2) and (D3) are situated within the region formed by the two LTRs joined together.

4. The plasmid vector according to claim 1, wherein a DNA segment encoding a nuclear localization signal is further added to the integrase gene.

5. The plasmid vector according to claim 1, wherein the integrase gene is isolated from viruses belonging to Retroviridae.

6. The plasmid vector according to claim 5, wherein the viruses belonging to Retroviridae are from the subfamily Oncovirinae.

* * * * *

UNITED STATES PATENT AND TRADEMARK OFFICE
CERTIFICATE OF CORRECTION

PATENT NO. : 6,936,465 B1
APPLICATION NO. : 09/762,568
DATED : August 30, 2005
INVENTOR(S) : Katsumate et al.

It is certified that error appears in the above-identified patent and that said Letters Patent is hereby corrected as shown below:

At column 2, line 3, delete "therepy" and insert --therapy--
At column 2, line 18, delete "(1983," and insert --(1983)--
At column 2, line 18, delete "p." and insert --pp.--
At column 2, line 19, delete "(1993," and insert --(1993)--
At column 2, line 19, delete "251." and insert --251,--
At column 2, line 19, delete "p." and insert --pp.--
At column 2, line 34, after "et al." insert --,--
At column 2, line 36, after "viruses" insert --.--
At column 2, line 44 delete "Makota" and insert --Makoto--
At column 5, line 49 delete "T" and insert --T.--
At column 5, line 51 delete "T" and insert --T.--
At column 5, line 51 delete "160." and insert --160,--
At column 5, line 55 delete "to," an insert --to--
At column 6, line 16, delete "et al.,J" and insert --et al., J.--
At column 7, line 35, after "Tanaka et al" insert --.--
At column 7, line 49, delete "occured" and insert --occurred--
At column 8, line 13, delete "develop" and insert --developing a--
At column 12, line 15, delete "Virolog," and insert --Virology,--
At column 13, line 8, delete "Nat." and insert --Natl.--
At column 13, line 38, delete "T", and insert --T.--
At column 13, line 39, delete "Duyk." and insert --Duyk,--
At column 15, line 3, delete "hybridyzation" and insert --hybridization--
At column 16, line 7, delete "Into" and insert --into--
At column 21, line 49, delete "L," and insert --L.--
At column 21, line 56, delete "powder sand" and insert --powders and--
At column 22, line 28, delete "integerate" and insert --integrate--
At column 27, line 22, delete ""RSV"" and insert -- "RSV,"--
At column 28, line 29, delete "J," and insert --J.--
At column 28, line 48, delete "998." and insert --998,--
At column 32, line 61, after "the" delete "a"
At column 35, line 41, delete "vecter" and insert --vector--
At column 35, line 1, below "<160>" insert --<170> SOFTWARE: FastSEQ for Windows Version 4.0-

UNITED STATES PATENT AND TRADEMARK OFFICE
CERTIFICATE OF CORRECTION

PATENT NO.       : 6,936,465 B1
APPLICATION NO.  : 09/762568
DATED            : August 30, 2005
INVENTOR(S)      : Katsumate et al.

It is certified that error appears in the above-identified patent and that said Letters Patent is hereby corrected as shown below:

At column 41, line 53, delete "ofNheI" and insert --of NheI--
At column 43, line 15, delete "vecter" and insert --vector--

Signed and Sealed this

Eighth Day of August, 2006

JON W. DUDAS
*Director of the United States Patent and Trademark Office*